US007718413B2

(12) United States Patent
Anderson et al.

(10) Patent No.: US 7,718,413 B2
(45) Date of Patent: May 18, 2010

(54) GLYCOSYLATION VARIANTS OF BACE

(75) Inventors: John Anderson, San Francisco, CA (US); Lisa McConlogue, Burlingame, CA (US); Guriqbal Basi, Palo Alto, CA (US); Sukanto Sinha, San Francisco, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 12/341,336

(22) Filed: Dec. 22, 2008

(65) Prior Publication Data
US 2009/0286281 A1 Nov. 19, 2009

Related U.S. Application Data

(63) Continuation of application No. 10/837,021, filed on Apr. 30, 2004, now Pat. No. 7,482,136.

(60) Provisional application No. 60/467,509, filed on May 2, 2003.

(51) Int. Cl.
C12N 9/50 (2006.01)
C12N 1/20 (2006.01)
C12N 15/00 (2006.01)
C07H 21/04 (2006.01)

(52) U.S. Cl. .................. 435/219; 435/226; 435/252.3; 435/325; 435/320.1; 536/23.2; 536/23.1

(58) Field of Classification Search ....................... None
See application file for complete search history.

(56) References Cited

U.S. PATENT DOCUMENTS

| 5,744,346 A | 4/1998 | Chrysler et al. |
| 6,319,689 B1 | 11/2001 | Powell et al. |

FOREIGN PATENT DOCUMENTS

| WO | 9822597 | 5/1998 |
| WO | 0017369 | 3/2000 |
| WO | 0047618 | 8/2000 |
| WO | 0100663 | 1/2001 |
| WO | 0123533 | 4/2001 |
| WO | 03012089 | 2/2003 |

OTHER PUBLICATIONS

Yan, Riqiang, et al; *Membrane-anchored aspartyl protease with Alzheimer's disease β secretase activity*; Nature, vol. 402, pp. 533-537, Dec. 2, 1999.
Vassar, Robert, et al; *β-Secretase Cleavage of Alzheimer's Amyloid Precursor Protein by the Transmembrane Aspartic Protease BACE*; Science, vol. 286, pp. 733-741, Oct. 22, 1999.
Sinha, Sukanto, et al; *Purification and cloning of amyloid precursor protein β-secretase from human brain*; Nature, vol. 402, 537-540, Dec. 2, 1999.
Mallender, William; *Characterization of Recombinant, Soluble β-Secretase from an Insect Cell Expression System*; Molecular Pharmacology, vol. 59, No. 3, pp. 619-626, 2001.
Benjannet, Suzanne, et al; *Post-translational Processing of β-Secretase (β-Amyloid-converting Enzyme) and its Ectodomain Shedding*; The Journal of Biological Chemistry, vol. 276, No. 14, 10879-10887, Apr. 6, 2001.
Capell, Anja, et al; *Maturation of Pro-peptide Cleavage of β-Secretase*; The Journal of Biological Chemistry, vol. 275, No. 40, pp. 30849-30854, Oct. 6, 2000.
Charlwood, Joanne, et al; *Characterization of the Glycosylation Profiles of Alzheimer's β-Secretase Protein Asp-2 Expressed in a Variety of Cell Lines*; The Journal of Biooilogical Chemistry, vol. 276, No. 20, p. 16739-16748, May 18, 2001.
Ermolieff, Jacques, et al; *Proteolytic Activation of Recombiant Promemapsin 2(Pro-β-secretase) Studied with new Fluorogenic Substrates*; Biochemistry, vol. 39, pp. 12450-12456, 2000.
Haniu, Mitsuru, et al; *Chracterization of Alzheimer's β-Secretase Protein BACE*; The Journal of Biological Chemistry; vol. 275, No. 28, pp. 21099-21106, Jul. 14, 2000.
Hussain, Ishrut, et al; *Identification of a Novel Aspartic Protease (Asp 2) as β-Secretase*; Molecular and Cellular, Neuroscience; vol. 14, pp. 419-427, 1999.
Lin, Xinli, et al; *Human aspartic proteasemeapsin 2 cleaves the β-amyloid precursor protein*; PNAS, vol. 97, pp. 1456-1460, Feb. 15, 2000.
Selkoe, D.J.; *Cell Biology of the β-Amyloid Precursor Protein and the Genetics of alzheimer's Disease*; Cold Spring Harbor Symposia on Quantatative Biology, vol. LXI, pp. 587-596, 1996.
Selkoe, Dennis J.; *Translating cell biology into therapeutic advances in Alzheimer's disease*; Nature, vol. 399 (supp), pp. A23-A31, Jun. 24, 1999.
Thinakaran, Gopal, et al; *Metabolism of the "Swedish" Amyloid Precursor Protein Variant in Neuro2a (N2a) Cells*; the Journal of Biological Chemistry; vol. 271, No. 16, pp. 9390-9397, Apr. 19, 1996.
Shi, Siao-Ping, et al; *The Pro Domain of B-Secretase does not Confer Strict Zymogen-like Properties but Does Assit Proper Folding of the Protease Domain*; vol. 276, No. 13, pp. 10366-10373, 2001.
Hong, Lin, et al; *Structure of the Protease Domain of Memapsin2 (B-Secretase) Complexed with Inhibitor*, Science Magazine, vol. 290, pp. 150-153, Oct. 6, 2000.
Selkoe, Dennis, J.; *Alzheimer's Disease; Genes, Proteins and Therapy*, Physiological Review, vol. 81, No. 2, pp. 741-766, Apr. 2001.
Farzan, M., et al, *BACE2, a beta-secretase homolog, cleaves at the beta site and within the amyloid-beta region of the amyloid beta precursor protein*, Proc. Natl. Acad. Sci., vol. 97, pp. 9712-0717, 2000.

*Primary Examiner*—Nashaat T Nashed
(74) *Attorney, Agent, or Firm*—McDonnell Boehnen Hulbert & Berghoff, LLP

(57) ABSTRACT

Human BACE polypeptides having modifications to the N-linked glycosylation sites including one or more of the following amino acid substitutions: S174I, N223A, N153Q and N354S. DNA sequences, vectors, and host cells for producing the polypeptides. Crystalline protein compositions formed from the purified polypeptides. Methods of screening for compounds that inhibit Aβ using the polypeptides.

14 Claims, 6 Drawing Sheets

FIG. 1

Amino Acid Sequence of Human BACE [SEQ ID NO:1]

| | | | | | |
|---|---|---|---|---|---|
| *MAQALPWLLL* | *WMGAGVLPAH* | *G*TQHGIRLPL | RSGLGGAPLG | LRLPRETDEE | 50 |
| PEEPGRRGSF | VEMVDNLRGK | SGQGYYVEMT | VGSPPQTLNI | LVDTGSSNFA | 100 |
| VGAAPHPFLH | RYYQRQLSST | YRDLRKGVYV | PYTQGKWEGE | LGTDLVSIPH | 150 |
| GPNVTVRANI | AAITESDKFF | INGSNWEGIL | GLAYAEIARP | DDSLEPFFDS | 200 |
| LVKQTHVPNL | FSLQLCGAGF | PLNQSEVLAS | VGGSMIIGGI | DHSLYTGSLW | 250 |
| YTPIRREWYY | EVIIVRVEIN | GQDLKMDCKE | YNYDKSIVDS | GTTNLRLPKK | 300 |
| VFEAAVKSIK | AASSTEKFPD | GFWLGEQLVC | WQAGTTPWNI | FPVISLYLMG | 350 |
| EVTNQSFRIT | ILPQQYLRPV | EDVATSQDDC | YKFAISQSST | GTVMGAVIME | 400 |
| GFYVVFDRAR | KRIGFAVSAC | HVHDEFRTAA | VEGPFVTLDM | EDCGYNIPQT | 450 |
| DESTLMTIAY | VMAAICALFM | LPLCLMVCQW | RCLRCLRQQH | DDFADDISLLK | 501 |

```
                                                            ETDEE    50
PEEPGRRGSF  VEMVDNLRGK  SGQGYYVEMT  VGSPPQTLNI  LVDTGSSNFA  100
VGAAPHPFLH  RYYQRQLSST  YRDLRKGVYV  PYTQGKWEGE  LGTDLVSIPH  150
GPNVTVRANI  AAITESDKFF  INGSNWEGIL  GLAYAEIARP  DDSLEPFFDS  200
LVKQTHVPNL  FSLQLCGAGF  PLAQSEVLAS  VGGSMIIGGI  DHSLYTGSLW  250
YTPIRREWYY  EVIIVRVEIN  GQDLKMDCKE  YNYDKSIVDS  GTTNLRLPKK  300
VFEAAVKSIK  AASSTEKFPD  GFWLGEQLVC  WQAGTTPWNI  FPVISLYLMG  350
EVTNQSFRIT  ILPQQYLRPV  EDVATSQDDC  YKFAISQSST  GTVMGAVIME  400
GFYVVFDRAR  KRIGFAVSAC  HVHDEFRTAA  VEGPFVTLDM  EDCGYNIPQT  450
D           (SEQ ID NO:2)                                   451
```

FIG. 3

S174I and N223A (Δ2,3)

```
                                                    ETDEE    50
PEEPGRRGSF VEMVDNLRGK SGQGYYVEMT VGSPPQTLNI LVDTGSSNFA   100
VGAAPHPFLH RYYQRQLSST YRDLRKGVYV PYTQGKWEGE LGTDLVSIPH   150
GPNVTVRANI AAITESDKFF INGINWEGIL GLAYAEIARP DDSLEPFFDS   200
LVKQTHVPNL FSLQLCGAGF PLAQSEVLAS VGGSMIIGGI DHSLYTGSLW   250
YTPIRREWYY EVIIVRVEIN GQDLKMDCKE YNYDKSIVDS GTTNLRLPKK   300
VFEAAVKSIK AASSTEKFPD GFWLGEQLVC WQAGTTPWNI FPVISLYLMG   350
EVTNQSFRIT ILPQQYLRPV EDVATSQDDC YKFAISQSST GTVMGAVIME   400
GFYVVFDRAR KRIGFAVSAC HVHDEFRTAA VEGPFVTLDM EDCGYNIPQT   450
D          (SEQ ID NO:3)                                451
```

FIG. 4

N153Q, S174I and N223A (Δ1,2,3)

|  |  |  |  |  |  |
|---|---|---|---|---|---|
|  |  |  |  | ETDEE | 50 |
| PEEPGRRGSF | VEMVDNLRGK | SGQGYYVEMT | VGSPPQTLNI | LVDTGSSNFA | 100 |
| VGAAPHPFLH | RYYQRQLSST | YRDLRKGVYV | PYTQGKWEGE | LGTDLVSIPH | 150 |
| GPQVTVRANI | AAITESDKFF | INGINWEGIL | GLAYAEIARP | DDSLEPFFDS | 200 |
| LVKQTHVPNL | FSLQLCGAGF | PLAQSEVLAS | VGGSMIIGGI | DHSLYTGSLW | 250 |
| YTPIRREWYY | EVIIVRVEIN | GQDLKMDCKE | YNYDKSIVDS | GTTNLRLPKK | 300 |
| VFEAAVKSIK | AASSTEKFPD | GFWLGEQLVC | WQAGTTPWNI | FPVISLYLMG | 350 |
| EVTNQSFRIT | ILPQQYLRPV | EDVATSQDDC | YKFAISQSST | GTVMGAVIME | 400 |
| GFYVVFDRAR | KRIGFAVSAC | HVHDEFRTAA | VEGPFVTLDM | EDCGYNIPQT | 450 |
| D | (SEQ ID NO:4) |  |  |  | 451 |

FIG. 5

N153Q, S174I, N223A and N354S (Δ1,2,3,4)

```
                                                        ETDEE    50
PEEPGRRGSF VEMVDNLRGK SGQGYYVEMT VGSPPQTLNI LVDTGSSNFA  100
VGAAPHPFLH RYYQRQLSST YRDLRKGVYV PYTQGKWEGE LGTDLVSIPH  150
GPQVTVRANI AAITESDKFF INGINWEGIL GLAYAEIARP DDSLEPFFDS  200
LVKQTHVPNL FSLQLCGAGF PLAQSEVLAS VGGSMIIGGI DHSLYTGSLW  250
YTPIRREWYY EVIIVRVEIN GQDLKMDCKE YNYDKSIVDS GTTNLRLPKK  300
VFEAAVKSIK AASSTEKFPD GFWLGEQLVC WQAGTTPWNI FPVISLYLMG  350
EVTSQSFRIT ILPQQYLRPV EDVATSQDDC YKFAISQSST GTVMGAVIME  400
GFYVVFDRAR KRIGFAVSAC HVHDEFRTAA VEGPFVTLDM EDCGYNIPQT  450
D          (SEQ ID NO:5)                                451
```

GLYCOSYLATION VARIANTS OF BACE

CROSS REFERENCE TO RELATED APPLICATION

This application is a divisional of U.S. patent application Ser. No. 10/837,021, filed Apr. 30, 2004, now U.S. Pat. No. 7,482,136, which claims the benefit of U.S. Provisional Patent Application Ser. No. 60/467,509 filed May 2, 2003, each of which is incorporated by reference herein in their entirety.

FIELD OF THE INVENTION

The invention is related to recombinant human BACE. More particularly, the invention is related to human BACE having modifications to the N-linked glycosylation sites.

BACKGROUND OF THE INVENTION

Neuritic plaques containing primarily amyloid beta protein (Abeta or Aβ) are one of the hallmarks of Alzheimer's Disease. Beta-site APP cleaving enzyme (BACE), known also as beta-secretase, β-secretase, Asp2, and Memapsin, has been identified as the enzyme responsible for processing amyloid precursor protein (APP) to produce the N-terminal portion of the Abeta peptide. This enzyme has been suggested as rate limiting in the production of the Abeta peptide. See, for example, Sinha et al., 1999, *Nature* 402:537-554, and published PCT applications WO 00/17369, WO 01/23533, and WO 00/47618. See also: Hussain, I. et al., 1999, *Mol. Cell. Neurosci.* 14:419-427; Vassar, R. et al., 1999, *Science* 286:735-741; Yan, R. et al., 2000, *Nature* 402:533-537; and Lin, X. et al., 2000, *Proc. Natl. Acad. Sci. USA* 97:1456-1460 (2000).

BACE is a relatively large and structurally complex enzyme. The primary structure of BACE as it is synthesized in the endoplasmic reticulum is shown in FIG. 1. The enzyme contains 501 amino acids, including a N-terminal signal (leader) sequence of about 21 amino acids (pre-sequence domain) followed by a pro-sequence domain consisting approximately of residues 22 to 45 (pro-sequence domain) that is proteolytically removed once the enzyme reaches its destination in the Golgi apparatus, to generate a mature enzyme.

BACE contains a transmembrane domain of about 27 amino acids that anchors the protein to the membrane. A short cytosolic C-terminal tail of 21 amino acids follows the transmembrane domain. Attachment to the membrane allows BACE to interact with and cleave APP, the first and prerequisite step in the generation of A-beta.

BACE isolated from human brain is heavily glycosylated. As expressed by a stably transfected 293T cell line, BACE is glycosylated at four asparagines: 132, 151, 202, and 333. Analysis of HEK 293 cells stably overexpressing BACE showed that the enzyme is phosphorylated at Ser477, and that phosphorylation regulates enzyme intracellular trafficing (Walter et. al., 2001, *J. Biol. Chem.* 276:14634-41). Three disulfide bonds suggested as critical for activity, are formed between the following pairs of cysteine residues: Cys216-Cys420, Cys278-Cys443, and Cys330-Cys380 (Haniu et. al., 2000, *J. Biol. Chem.* 275:21099-21106).

These structural features of the BACE polypeptide all appear to have specific functions relating to enzymatic activity. Enzymes expressed in insect and CHO cells are properly refolded and show activity. These proteins are glycosylated. For example, insect cells express glycosylated BACE from the mannose-rich glycans available in the insect cells. Biantennary and triantennary oligosaccharides of the complex type provide glycosylation in the CHO-expressed BACE (Charlwood et. al., 2001 *J. Biol. Chem.* 276:16739-48).

Published patent applications WO 00/47618, WO 01/23533 and WO 00/17369 identify the beta-secretase enzyme and various methods of its use. To better understand the mechanism of action of β-secretase and help explore novel strategies for drug discovery for Alzheimer's disease, it has become important to understand the role of the four N-linked glycosylation sites of BACE. This understanding will make it possible to explore mutations in BACE that enzyme activity as well as explore potential active sites for target molecules.

SUMMARY OF THE INVENTION

In one aspect, the invention is directed to isolated polypeptide having the amino acid sequence of a BACE polypeptide having at least one of the following amino acid substitutions: S174I, N223A, N153Q and N354S. Examples of these sequences are shown in SEQ ID NO:2 and SEQ ID NO:3. The sequence may have a C-terminus selected from a residue between 452 and 501. In addition, the sequence may have an N terminal residue corresponding to residue position 46, or an N terminus having amino acids NINL (SEQ ID NO:13) at positions 42-45.

In another aspect, the invention is directed to an isolated protein with a polypeptide that (i) is less than about 450 amino acid residues in length; (ii) is at least 90% identical to any one of SEQ ID NOs:2-5 of the invention, including conservative substitutions thereof, wherein the glycosylation sites are identical to those of SEQ ID NOs: 2-5 and (iii) exhibits β-secretase activity by an ability to cleave a substrate MBP-C125Swe. The polypeptide may be at least 95% identical to any one of SEQ ID NOs:2-5. In yet another aspect, the invention is directed to a crystalline protein composition formed from the purified polypeptide of the invention.

Further, the invention is directed to a method for screening for compounds that inhibit the production of Aβ where the method includes contacting an isolated polypeptide of the invention with (a) test compound and (ii) a β-secretase substrate, and selecting the test compound as capable of inhibiting Aβ production if the polypeptide exhibits less β-secretase activity in the presence of the compound than in the absence of the compound.

Still further, the invention is directed to a method of screening compounds that inhibit Aβ production where the method includes measuring binding of a purified β-secretase polypeptide of the invention with a β-secretase inhibitor compound in the presence of a test compound, and selecting the test compound as an inhibitor of Aβ production if the binding of the inhibitor in the presence of the test compound is less than the binding of the inhibitor in the absence of the test compound. The inhibitor may be P10-4'staD→V.

In other aspects, the invention is directed to a purified and isolated DNA sequence that, by virtue of the degeneracy of the genetic code, encodes any of the polypeptides of the invention. Expression vectors, host cells and methods of producing the polypeptide are included.

BRIEF DESCRIPTION OF THE FIGURES

FIG. 1 shows the amino acid sequence of Human BACE [SEQ ID NO: 1].

FIG. 2 is an amino acid sequence of the present invention referred to herein as Δ3 wherein the amino acid corresponding to position 223 of wild type BACE has been changed from asparagine to alanine (N223A) [SEQ ID NO: 2].

FIG. 3 is an amino acid sequence of the present invention referred to herein as Δ2,3 wherein the amino acids corresponding to positions 174 and 223 of wild type BACE have been changed from serine to isoleucine (S174I) and asparagine to alanine (N223A) [SEQ ID NO: 3].

FIG. 4 is an amino acid sequence of the present invention referred to herein as Δ1,2,3 wherein the amino acids corresponding to positions 153, 174 and 223 of wild type BACE have been changed from asparagine to glutamine (N153Q), serine to isoleucine (S174I) and asparagine to alanine (N223A) [SEQ ID NO: 4].

FIG. 5 is an amino acid sequence of the present invention referred to herein as Δ1,2,3,4 wherein the amino acids corresponding to positions 153, 174, 223 and 354 of wild type BACE have been changed from asparagine to glutamine (N153Q), serine to isoleucine (S174I), asparagine to alanine (N223A), and asparagine to serine (N354S) [SEQ ID NO: 5].

DETAILED DESCRIPTION

Figure 6:
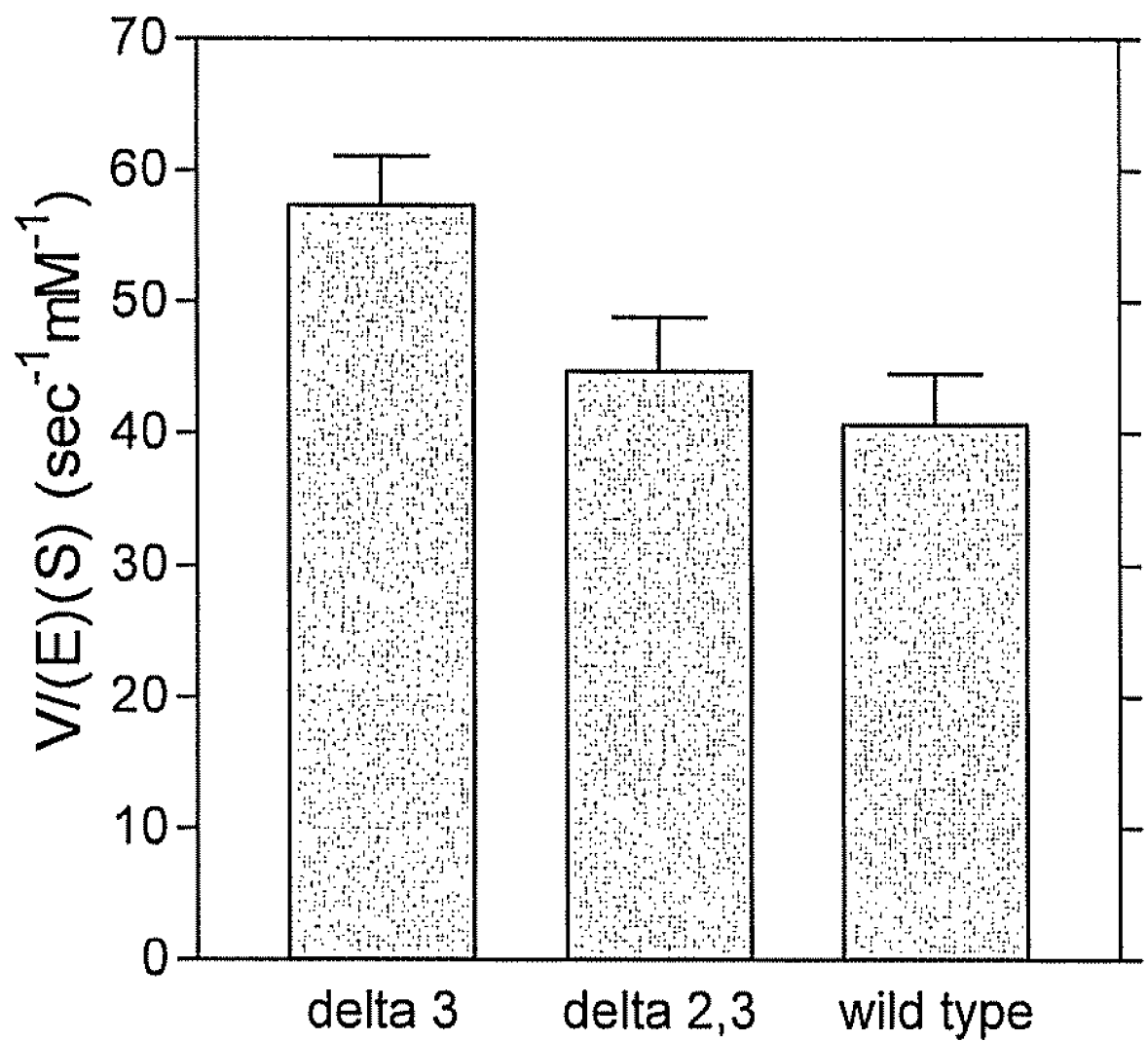
FIG. 6 is a graph showing the results of assays comparing the activity of BACE variants having deleted glycosylation sites compared with fully glycosylated BACE against substrate MBP-C125$_{Swe}$. Activity is in pM product produced per second, per pM purified BACE, per mM substrate.

Prior to describing the invention in detail, a number of terms will be defined. Unless otherwise indicated, all terms used herein have the same meaning as they would to one skilled in the art of the present invention. Practitioners are particularly directed to Sambrook, et al (1989) Molecular Cloning: A Laboratory Manual (Second Edition), Cold Spring Harbor Press, Plainview, N.Y. and Ausubel, F. M., et al (1998) Current Protocols in Molecular Biology, John Wiley & Sons, New York, N.Y., for definitions, terms of art and standard methods known in the art of molecular biology, particularly as it relates to the cloning protocols described herein. It is understood that this invention is not limited to the particular methodology, protocols, and reagents described, as these may be varied to produce the same result.

The terms "β-secretase" and "BACE" (beta-site APP-cleaving enzyme) are used interchangeably herein to refer to an enzyme that cleaves amyloid precursor protein (APP) between residues 596 and 597 (APP695 numbering convention) or 670 and 671 (APP770 numbering convention). Human and mouse forms of this enzyme has been cloned by a number of groups and reported to be a membrane-bound aspartyl protease. (Sinha, *Nature* 402: 537-540, 1999; Yan, *Nature* 402: 533-536, 1999; Vassar, *Science*, 286: 735-741, 1999). The sequences reported in these publications are alleles of the same gene. A second nonallelic form of beta-secretase has been described by published patent applications WO 00/17369, WO 00/47618 and WO 01/23533, each of which is incorporated herein by reference in its entirety, and Farzan et al., *Proc Natl Acad Sci USA*. 2000 Aug. 15; 97(17): 9712-717.

Features of the human BACE shown in FIG. 1 include a 21 amino acid leader (signal or pre-) sequence shown in italics, and a 24 amino acid pro-sequence, shown in bold type. A 27 amino acid transmembrane domain is underlined, and is followed by the cytosolic C-terminal tail. Disulphide bridges are formed by cysteines (Cys$^{216}$-Cys$^{420}$, Cys$^{278}$-Cys$^{443}$; and Cys$^{330}$-Cys$^{380}$).

The polypeptide has four N-linked glycosylation sites at Asn$^{53}$, Asn$^{172}$, Asn$^{223}$ and Asn$^{354}$ as shown in bold and enlarged print (N) in FIG. 1. The glycosylation sites of BACE are identified by the consensus sequences of -Asn-X-Ser- and -Asn-X-Thr-, where X is any of the normal amino acids except proline. The invention provides for a series of BACE variants created by the deletion of one or more of the four N-linked glycosylation sites of BACE. Deletion of the N-linked sites may be accomplished by mutation the consensus glycosylation site, for example, by replacing the asparagines, serine or threonine residues of the glycosylation site.

As used herein, BACE polypeptide refers to the polypeptide and fragments thereof that may optionally include the complete, or portions of the signal sequence, the pro sequence, the transmembrane domain, and/or the C-terminal tail. "A portion of" refers to any number of amino acids in the various sequences. In various aspects of the invention, the BACE polypeptide sequences are N-terminal and/or C-terminal truncated sequences of the BACE polypeptide, for example, polypeptides having residues 46-451, residues 46-453, residues 1-451, residues 22-451, residues 46-480, etc. In other aspects, the invention includes any number of amino acids of the BACE polypeptide sequence at the C-terminus and N-terminus of the truncated sequence.

The term "polypeptide" as used herein refers to a compound made up of a single chain of amino acid residues linked by peptide bonds. The term "protein" may be synonymous with the term "polypeptide" or may refer to a complex of two or more polypeptides.

The term "modified," when referring to a polypeptide of the invention, means a polypeptide which is modified either by natural processes, such as processing or other post-translational modifications, or by chemical modification techniques which are well known in the art. Among the numerous known modifications which may be present include, but are not limited to acetylation, acylation, amidation, ADP-ribosylation, glycosylation, GPI anchor formation, covalent attachment of lipid or lipid derivative, methylation, myristlyation, pegylation, prenylation, physphorylation, ubiqutination, or any similar process.

The term "biologically active" used in conjunction with the term β-secretase refers to possession of a β-secretase enzyme activity, such as the ability to cleave β-amyloid precursor protein (APP) to produce β-amyloid peptide (Aβ).

The term "fragment," when referring to β-secretase of the invention, means a polypeptide which as an amino acid sequence which is the same as part of but not all of the amino acid sequence of full-length β-secretase polypeptide. In the context of the present invention, β-secretase is generally identified as SEQ ID NO: 1 (the ORF of the full-length nucleotide); however, according to a to on aspect of the invention, the active form is one or more N-terminal truncated versions, such as amino acids 46-501, 22-501, 58-501 or 63-501; other active forms are C-terminal truncated forms ending between about amino acids 450 and 452. The numbering system used throughout is based on the numbering of the sequence SEQ ID NO: 1.

An "active fragment" is a β-secretase fragment that retains at least one of the functions or activities of β-secretase, including but not limited to the β-secretase enzyme activity discussed above and/or ability to bind to the inhibitor substrate described herein as P10-P4'staD→V (SEQ ID NO: 6). Fragments contemplated include, but are not limited to, a β-secretase fragment which retains the ability to cleave β-amyloid precursor protein to produce β-amyloid peptide. Such a fragment preferably includes at least 350, and more preferably at least 400, contiguous amino acids or conservative substitutions thereof of β-secretase, as described herein. More preferably, the fragment includes active aspartyl acid residues in the structural proximities identified and defined by the primary polypeptide structure shown as SEQ ID NO: 1 with the variations to the glycosylation sites described herein.

A "conservative substitution" refers to the substitution of an amino acid in one class by an amino acid in the same class, where a class is defined by common physicochemical amino acid side chain properties and high substitution frequencies in homologous proteins found in nature (as determined e.g., by a standard Dayhoff frequency exchange matrix or BLOSUM matrix). Six general classes of amino acid sidechains, categorized as described above, include Class I (Cys); Class II (Ser, Thr, Pro, Ala, Gly); Class III (Asn, Asp, Gln, Glu); Class IV (His, Arg, Lys); Class V (Ile, Leu, Val, Met): and Class VI (Phe, Tyr, Trp). For example, substitution of an Asp for another class III residue such as Asn, Gln, or Glu, is considered to be a conservative substitution.

"Optimal alignment" is defined as an alignment giving the highest percent identity score. Such alignment can be performed using a variety of commercially available sequence analysis programs, such as the local alignment program LALIGN using a ktup of 1, default parameters of the default PAM. A preferred alignment is the pairwise alignment using the CLUSTAL-W program in MacVector, operated with default parameters, including an open gap penalty of 10.0, an extended gap penalty of 0.1 and a BLOSUM30 similarity matrix.

"Percent sequence identity," with respect to two amino acid or polynucleotide sequences, refers to the percentage of residues that are identical in the two sequences when the sequences are optimally aligned. Thus 80% amino acid sequence identity means that 80% of the amino acids in two or more optimally aligned polypeptide sequences are identical. If a gap needs to be inserted into a first sequence to optimally align it with a second sequences, the percent identity is calculated using only the residues that are paired with a corresponding amino acid residue (i.e., the calculation does not consider residues in the second sequences that are in the "gap" of the first sequence).

A first polypeptide region is said to "correspond" to a second polypeptide region when the regions are essentially coextensive when the sequences containing the regions are aligned using a sequence alignment program, as above. Corresponding polypeptide regions typically contain a similar, if not identical, number of residues. It will be understood, however, that corresponding regions may contain insertions or deletions of residues with respect to one another, as well as some differences in their sequences.

A first polynucleotide region is said to "correspond" to a second polynucleotide region when the regions are essentially co-extensive when the sequences containing the regions are aligned using a sequence alignment program, as above. Corresponding polynucleotide regions typically contain a similar, if not identical, number of residues. It will be understood, however, that corresponding regions may contain insertions or deletions of basis with respect to one another, as well as some differences in their sequences.

The term "sequence identity" means nucleic acid or amino acid sequence identity in two or more aligned sequences, aligned as defined above.

"Sequence similarity" between two polypeptides is determined by comparing the amino acid sequence and its conserved amino acid substitutes of one polypeptide to the sequence of a second polypeptide. Thus, 80% protein sequence similarity means that 80% of the amino acid residues in two or more aligned protein sequences are conserved amino acid residues, i.e., are conservative substitutions.

The terms "polynucleotide" and "nucleic acid" are used interchangeably herein and refer to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

"Hybridization" includes any process by which a strand of nucleic acid joins with a complementary nucleic acid strand through base pairing. Thus, strictly speaking, the term refers to the ability of the complement of the target sequence to bind to the test sequence, or vice-versa.

"Hybridization conditions" are based in part on the melting temperature (TM) of the nucleic acid binding complex or probe and are typically classified by degree of "stringency" of the conditions under which hybridization is measured. The specific conditions that define various degrees of stringency (i.e., high, medium, low) depend on the nature of the polynucleotide to which hybridization is desired, particularly its percent GC content, and can be determined empirically according to methods known in the art. Functionally, maximum stringency conditions may be used to identify nucleic acid sequences having strict identity with the hybridization probe; while high stringency conditions are used to identify nucleic acid sequences having about 80% or more sequence identity with the probe.

The term "gene" as used herein means the segment of DNA involved in producing a polypeptide chain; it may include regions preceding and following the coding region, e.g., 5' untranslated (5' UTR) or "leader" sequences and 3' UTR or "trailer" sequences, as well as intervening sequences (introns) between individual coding segments (exons).

The term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all the coexisting materials in the natural system, is isolated. Such isolated polynucleotides may be part of a vector and/or such polynucleotides or polypeptides may be part of a composition, such as recombinantly produced cells (heterologous cell) expressing the polypeptide, and still be isolated in that such vector or composition is not part of its natural environment.

An "isolated" as it applied to a polynucleotide sequence that encodes β-secretase" is a polynucleotide that contains the coding sequence of β-secretase, or an active fragment thereof, (i) alone, (ii) in combination with additional coding sequences, such as fusion protein or signal peptide, in which the β-secretase coding sequence is the dominant coding sequence, (iii) in combination with non-coding sequences, such as introns and control elements, such as promoter and terminator elements or 5' and/or 3' untranslated regions, effective for expression of the coding sequence in a suitable host, and/or (iv) in a vector or host environment in which the β-secretase coding sequence is a heterologous gene.

The terms "heterologous DNA," "heterologous RNA," "heterologous nucleic acid," "heterologous gene" and "heterologous polynucleotide" refer to nucleotides that are not endogenous to the cell or part of the genome in which they are present; generally such nucleotides have been added to the cell, by transfection, microinjection, electroporation, or the like. Such nucleotides generally include at least one coding sequence, but this coding sequence need not be expressed.

The term "heterologous cell" refers to a recombinantly produced cells that contains at least one heterologous DNA molecule.

A "recombinant protein" is a protein isolated, purified, or identified by virtue of expression in a heterologous cell, said cell having been transduced or transfected, either transiently or stably, with a recombinant expression vector engineered to drive expression of the protein in the host cell.

The term "expression" means that a protein is produced by a cell, usually as a result of transfection of the cell with a heterologous nucleic acid.

"Co-expression" is a process by which two or more proteins or RNA species of interest are expressed in a single cell. Co-expression of the two or more proteins is typically achieved by transfection of the cell with one or more recombinant expression vector(s) that carry coding sequences for the proteins. In the context of the present invention, for example, a cell can be said to "co-express" two proteins, if one or both of the proteins is heterologous to the cell.

The terms "vector" or "expression vector" refer to a polynucleotide having a nucleotide sequence that can assimilate new nucleic acids, and propagate those new sequences in an appropriate host, such as the ability to incorporate and express heterologous DNA fragments in a foreign cell. Vectors include, but are not limited to recombinant plasmids and viruses. The vector (e.g., plasmid or recombinant virus) comprising the nucleic acid of the invention can be in a carrier, for example, a plasmid complexed to protein, a plasmid complexed with lipid-based nucleic acid transduction systems, or other non-viral carrier systems. Selection of appropriate expression vectors is within the knowledge of those having skill in the art.

The terms "purified" or "substantially purified" refer to molecules, either polynucleotides or polypeptides, that are removed from their natural environment, isolated or separated, and are at least 90% and more preferably at least 95-99% free from other components with which they are naturally associated. The foregoing notwithstanding, such a descriptor does not preclude the presence in the same sample of splice- or other protein variants (glycosylation variants) in the same, otherwise homogeneous, sample.

A protein or polypeptide is generally considered to be "purified to apparent homogeneity" if a sample containing it shows a single protein band on a silver-stained polyacrylamide electrophoretic gel.

The term "crystallized protein" means a protein that has a co-precipitated out of solution. In pure crystals consisting only of the crystal, but possibly including other components that are tightly bound to the protein.

A "variant" polynucleotide sequence may encode a "variant" amino acid sequence that is altered by one or more amino acids from the reference polypeptide sequence. The variant polynucleotide sequence may encode a variant amino acid sequence, which contains "conservative" substitutions, wherein the substituted amino acid has structural or chemical properties similar to the amino acid which it replaces. In addition, or alternatively, the variant polynucleotide sequence may encode a variant amino acid sequence, which contains "non-conservative" substitutions, wherein the substituted amino acid has dissimilar structural or chemical properties to the amino acid which it replaces. Variant polynucleotides may also encode variant amino acid sequences, which contain amino acid insertions or deletions, or both. Furthermore, a variant polynucleotide may encode the same polypeptide as the reference polynucleotide sequence but, due to the degeneracy of the genetic code, has a polynucleotide sequence that is altered by one or more bases from the reference polynucleotide sequence.

An "allelic variant" is an alternate form of a polynucleotide sequence, which may have a substitution, deletion or addition of one or more nucleotides that does not substantially alter the function of the encoded polypeptide.

"Alternative splicing" is a process whereby multiple polypeptide isoforms are generated from a single gene, and involves the splicing together of nonconsecutive exons during the processing of some, but not all, transcripts of the gene. Thus, a particular exon may be connected to any one of several alternative exons to form messenger RNAs. The alternatively-spliced mRNAs produce polypeptides ("splice variants") in which some parts are common while other parts are different.

"Splice variants" of β-secretase, when referred to in the context of an mRNA transcript, are mRNAs produced by alternative splicing of coding regions, i.e., exons, from the β-secretase gene. "Splice variants" of β-secretase, when referred to in the context of the protein itself, are secretase translation products that are encoded by alternatively-spliced β-secretase mRNA transcripts.

A "mutant" amino acid or polynucleotide sequence is a variant amino acid sequence, or a variant polynucleotide sequence, which encodes a variant amino acid sequence that has significantly altered biological activity or function from that of the naturally occurring protein.

A "substitution" results from the replacement of one or more nucleotides or amino acids by different nucleotides or amino acids, respectively.

The term "modulate" as used herein refers to the change in activity of the polypeptide of the invention. Modulation may relate to an increase or a decrease in biological activity, binding characteristics, or any other biological, function, or immunological property of the molecule.

The terms "antagonist" and "inhibitor" are used interchangeably herein and refer to a molecule which, when bound to the polypeptide of the present invention, modulates the activity of enzyme by blocking, decreasing or shortening the duration of the biological activity. An antagonist as used herein may also be referred to as a "β-secretase inhibitor" or "β-secretase blocker." Antagonists may themselves be polypeptides, nucleic acids, carbohydrates, lipids, small molecules (usually less than 1000 kD), or derivatives thereof, or any other ligand which binds to and modulates the activity of enzyme.

In one aspect, the BACE polypeptide sequences of the invention have at least one of the four N-linked glycosylation sites deleted. Deletion of the sites may be accomplished by introducing a one or more of the following mutations into the wild-type BACE sequence shown in FIG. 1: N153Q, S174I, N223A, and N354S. Referring now to FIGS. 2-5, specific examples of these sequences have the following mutations and may be referred to as follows:

Δ3—N223A (FIG. 2, SEQ ID NO:2);

Δ2,3—S174I and N223A (FIG. 3, SEQ ID NO:3)

Δ1,2,3—N153Q, S174I, and N223A (FIG. 4, SEQ ID NO:4);

Δ1,2,3,4—N153Q, S174I, N223A, and N354S (FIG. 5, SEQ ID NO:5).

In another aspect of the invention, the sequences are truncated after residue 451 with residue 452 replaced by a Flag sequence followed by a stop codon, removing the transmembrane and cytoplasmic domains. These sequences are referred to herein as 452Flag sequences, e.g. Δ3-452Flag. In another aspect, the transmembrane region of the BACE polypeptide of the invention is replaced with a histidine tag. Such sequences are referred to herein as 452H sequences, e.g. Δ3-452H.

The importance of the four N-linked glycosylation sites was determined by attempting to express SEQ ID NOs: 2-5 in HEK-293 cells. Expression of Δ1,2,3-452Flag and Δ1,2,3,4-452Flag did not result in β-secretase production suggesting that glycosylation at the first and last sites may be important for proper folding in mammalian cells. In contrast expression of Δ3-452Flag and Δ2,3-452Flag resulted in secretion of soluble β-secretase at levels comparable to the fully glycosylated 452Flag. In activity assays directed against a bacterial fusion protein containing maltose binding protein (MBP) fused to the C-terminal 125 amino acids of the Swedish variant ($Lys_{670}Asn$, $Met_{671}Leu$ double mutation) of APP (referred to herein as MBP-C125$_{Swe}$), all three proteins (452 Flag, Δ3-452Flag and Δ2,3-452Flag) had similar specific activities, suggesting that at least two of the four N-linked glycosylation sites are not necessary for BACE stability or activity. Furthermore, N-terminal sequencing of these three sequences showed that the enzymes were processed from proform to mature protein to a similar extent.

In another aspect, the invention provides for BACE DNA constructs having sequences prepared by selective mutagenesis, encoding the amino acid sequences of the invention. Preparation of these DNA constructs can be accomplished by site directed mutagenesis of wild-type BACE by techniques well known to those of skill in the art. Recombinant BACE can be produced, for example, in HEK-293 cells or other suitable host cells, by expressing a construct that contains at least a portion of a cDNA encoding BACE, for example, encoding at least a portion of the amino acid sequence shown in FIG. 1. The construct can also contain additional nucleotide sequences that may, for example, assist in purification and/or expression of the recombinant polypeptide, as desired.

One aspect the invention provides for a minimally glycosylated, soluble BACE produced in a baculovirus expression system. Mutant forms that may be expressed in this system include a BACE polypeptide that lacks one or more of the glycosylation sites, including any of the sequences of FIGS. 2-5. In a particular aspect of the invention, the mutant Δ2,3 having a Histidine tag in place of the transmembrane domain, known as Δ2,3-452H, was produced by inserting an polynucleotide sequence encoding the mutant into a baculovirus expression vector pVL1392 and expressing the sequence in Sf9 cells.

In addition, to increase the homogeneity of BACE molecules produced in a baculovirus expression system, a NINL (SEQ ID NO:13) mutation was introduced at the pro-sequence cleavage site $R_{42}L_{43}P_{44}R_{45}$. The (SEQ ID NO:13) mutation changes the amino acid sequence at the cleavage site from $R_{42}L_{43}P_{44}R_{45}$ to (SEQ ID NO:13). This mutation allows for the efficient cleavage at both the normal pro-region processing site and at a site 4 amino acids upstream, resulting in material with low to undetectable levels of unprocessed BACE protein. Although this is a heterogeneous mixture, the two forms generated using the NINL (SEQ ID NO:13) mutation differ by only 4 amino acids. This small difference in size provides a superior material for generating crystals compared to the material such as the wildtype BACE which generates a mixture of fully processed BACE with BACE containing the entire 45 amino acid pro-region. Thus, the NINL (SEQ ID NO:13) mutation provides a relatively homogeneous source of BACE protein without the pro-region.

The present invention provides an isolated, active human β-secretase enzyme, which is further characterized as an aspartyl (aspartic) protease or proteinase, optionally, in purified form. As defined more fully β-secretase exhibits a proteolytic activity that is involved in the generation of β-amyloid peptide from β-amyloid precursor protein (APP), such as is described in U.S. Pat. No. 5,744,346, incorporated herein by reference in its entirety. Alternatively, or in addition, the β-secretase is characterized by its ability to bind, with moderately high affinity, to an inhibitor substrate described herein as P10-P4'staD→V having the sequence KTEEISEVN[sta] VAEF (SEQ ID NO: 6) wherein sta is a statine molecule. The procedure for making this polypeptide in provided in Example 7 of U.S. Pat. No. 6,627,739, which is incorporated herein by reference in its entirety.

According to another aspect of the invention, nucleotide sequences encoding the mutant forms of the enzyme have been identified. In addition, the enzyme may be further modified for expression in altered forms, such as truncated forms, which have similar protease activity to the mutant or naturally occurring recombinant enzyme. Using the information provided herein, practitioners can isolate DNA encoding various active forms of the protein from available sources and can express the protein recombinantly in a convenient expression system.

β-secretase is of particular interest due to its activity and involvement in generating fibril peptide components that are the major components of amyloid plaques in the central nervous system (CNS), such as are seen in Alzheimer's disease, Down's syndrome and other CNS disorders. Accordingly, a useful feature of the present invention includes an isolated form of the enzyme that can be used, for example, to screen for inhibitor substances which are candidates for therapeutics for such disorders.

Glycosylation site variants of β-secretase as described herein can be used as starting material to determine a crystallographic structure and coordinates for the enzyme. Although any of the various forms of BACE described herein can be used for crystallization studies, minimally glycosylated forms of BACE are expected to provide a more uniform molecule that is easier to crystallize than fully glycosylated forms. Such structural determinations are particularly useful in defining the conformation and size of the substrate binding site. This information can be used in the design and modeling of substrate inhibitors of the enzyme. As discussed herein, such inhibitors are candidate molecules for therapeutics for treatment of Alzheimer's disease and other amyloid diseases characterized by Aβ peptide amyloid deposits.

The crystallographic structure of β-secretase is determined by first crystallizing the purified protein. Methods for crystallizing proteins, and particularly proteases, are now well known in the art. The practitioner is referred to *Principles of Protein X-ray Crystallography* (J. Drenth, Springer Verlag, NY 1999) for general principles of crystallography. Additional, kits for generating protein crystals are generally available from commercial providers, such as Hampton Research (Laguna Niguel, Calif.). Additional guidance can be obtained from numerous research articles that have been written in the area of crystallography of protease inhibitors, especially with respect to HIV-1 and HIV-2 proteases, which are aspartic acid proteases.

Although any of the various forms of β-secretase described herein can be used for crystallization studies, in on aspect, the β-secretase lacks the first 45 amino acids of the sequence shown as SEQ ID NO: 1, since this appears to be the predominant form which occurs naturally in human brain. It is thought that some form of post-translational modification, possible autocatalysis, serves to remove the first 45 amino acids in fairly rapid order, since, to date, virtually no naturally occurring enzymes has been isolated with all of the first 45 amino acids intact. In another aspect of the invention, the putative transmembrane region is removed from the molecule prior to crystallization, since this region is not necessary for catalysis and potentially could render the molecule more difficult to crystallize.

Thus, a good candidate for crystallization is β-secretase variant forms having polypeptides 46-451, since the natural form of this fragment of the enzyme (a) provides the predominant naturally occurring N-terminus, and (b) lacks the "sticky" transmembrane regions, while (c) retaining β-secretase activity. Alternatively, forms of the enzyme having extensions that extend part of the way (approximately 10-15 amino acids) into the transmembrane domain may also be used. In general, for determining X-ray crystallographic coordinates of the ligand binding site, any form of the enzyme can be used that either (i) exhibits β-secretase activity, and/or (ii) binds to a known inhibitor, such as the inhibitor ligand P10-P4'staD→V, with a binding affinity that is at least $\frac{1}{100}$ the binding affinity of β-secretase [46-501] to P10-P4'staD→V. Therefore, a number of additional truncated forms of the enzyme can be used in these studies. Suitability of any particular form can be assessed by contacting it with a P10-P4'staD→V affinity matrix. Truncated forms of the enzyme that bind to the matrix are suitable for such further analysis. Thus, in addition to 46-451, experiments have revealed that a naturally occurring β-secretase in truncated form ending in residue 419, most likely 46-419, also binds to the affinity matrix and is therefore is a possible an alternate candidate protein composition for X-ray crystallographic analysis mutant forms of β-secretase. More generally, any form of the enzyme that ends before the transmembrane domain, particularly those ending between about residue 419 and 452 are suitable in this regard.

At the N-terminus, as described above, generally the first 45 amino acids will be removed during cellular processing. Other naturally occurring or expressed forms are known. These include, for example, a protein commencing at residue 22, one commencing at residue 58 and one commencing at residue 63. However, analysis of the entire enzyme, starting at residue 1, can also provide information about the enzyme. Other forms, such as 1-420 to 1-452, including intermediate forms, for example 1-440, can be useful in this regard. The NINL (SEQ ID NO:13) pro-region mutation generates forms starting at 46 and 42. Structures of this mixture of forms would also be informative. In general, it will also be useful to obtain structure on any subdomain of the active enzyme.

Methods for purifying the protein, including active forms, are known. In addition, since the protein is apparently glycosylated in its naturally occurring (and mammalian-expressed recombinant) forms, it may be desirable to express the mutant proteins described herein and purify them from bacterial sources, which do not glycosylate mammalian proteins, or express the mutant proteins in sources, such as insect cells, that provide uniform glycosylation patterns, in order to obtain a homogeneous composition for those glycosylation sites that have not been removed in some aspects of the invention. Appropriate vectors and codon optimization procedures for accomplishing this are known in the art.

Following expression and purification, the protein is adjusted to a concentration of about 1-20 mg/ml. In accordance with methods that have worked for other crystallized proteins, the buffer and salt concentrations present in the initial protein solution are reduced to as low a level as possible. This can be accomplished by dialyzing the sample against the starting buffer, using microdialysis techniques known in the art. Buffers and crystallization conditions will vary from protein to protein, and possibly from fragment to fragment of the active β-secretase molecule, but can be determined empirically using, for example, matrix methods for determining optimal crystallization conditions. (Drentz, J., supra; Ducruix, A., et al, eds. *Crystallization of Nucleic Acids and Proteins: A practical Approach*, Oxford University Press, New York, 1992.)

Following dialysis, conditions may be optimized for crystallization of the protein. Generally, methods for optimization may include making a "grid" of 1 µl drops of the protein solution, mixed with 1 µl well solution, which is a buffer of varying pH and ionic strength. These drops are placed in individual sealed wells, typically in a "hanging drop" configuration, for example in commercially available containers (Hampton Research, Laguna Niguel, Calif.). Precipitation/crystallization typically occurs between 2 days and 2 weeks. Wells are checked for evidence of precipitation or crystallization and conditions are optimized to form crystals. Optimized crystals are not judged by size or morphology but rather by the diffraction quality of crystals, which should better than 3 Å resolution. Typical precipitating agents include ammonium sulfate ($NH_1SO_4$), polyethylene glycol (PEG) and methyl pentane diol (MPD). All chemicals used should be the highest grade possible (e.g., ACS) and may also be re-purified by standard methods known in the art, prior to use.

Exemplary buffers and precipitants forming an empirical grid for determining crystallization conditions are commercially available. For example, the "Crystal Screen" kit (Hampton Research) provides a sparse matrix method of trial conditions that is biased and selected from known crystallization conditions for macromolecules. This provides a "grid" for quickly treating wide ranges of pH, salts, and precipitants using a very small sample (50 to 100 microliters) of macromolecule. In such studies 1 µl of buffer/precipitant(s) solution is added to an equal volume of dialyzed protein solution, and the mixtures are allowed to sit for at least two days to two weeks, with careful monitoring of crystallization. Chemicals can be obtained from common commercial suppliers; however, it is preferable to use purity grades suitable for crystallization studies, such as are supplied by Hampton Research (Laguna Niguel, Calif.). Common buffers include Citrate, TEA, CHES, Acetate, ADA and the like (to provide a range of pH optima), typically at a concentration of about 100 mM. Typical precipitants include $(NH_4)_2SO_4$, $MgSO_4$, NaCl, MPD, ethanol, polyethylene glycol of various sizes, isopropanol, KCl; and the like (Ducruix).

Various additives can be used to aid in improving the character of the crystals, including substrate analogs, ligands, or inhibitors, as discussed in Part 2, below, as well as certain additives, including, but not limited to:

5% Jeffamine

5% Polypropyleneglycol P400

5% Polyethyleneglycol 400

5% ethyleneglycol

5% 2-methyl-2,4-pentamediol

5% Glycerol

5% Dioxane

5% dimethyl sulfoxide

5% n-Octanol 100 mM (Nh4)2SO4

100 mM CsCl 100 mM CoSO4

100 mM MnCl2

100 mM KCl 100 mM ZnSO4

100 mM LiCl2

100 mM MgCl2

100 mM Glucose 100 mM 1,6-Hexanediol 100 mM Dextran Sulfate 100 mM 1,6 hexane diamine 100 mM 1,8 diamino octane 100 mM Spermidine 100 mM spermic 0.17 mM n-dodecyl-β-D maltoside NP 40

20 mM n-octyl-β-D-glucopyranoside

The full-length β-secretase enzyme contains at least one transmembrane domain, and its purification is aided by the use of a detergent (Triton X-100). Membrane proteins can be crystallized intact, but may require specialized conditions, such as the addition of a non-ionic detergent, such as $C_8G$ (8-allyl-β-glucoside) or an n-alkyl-maltoside ($C_nM$). Selection of such a detergent is somewhat empirical, but certain detergents are commonly employed. A number of membrane proteins have been successfully "salted out" by addition of high salt concentrations to the mixture. PEG has also been used successfully to precipitate a number of membrane proteins (Ducruix, et al., supra).

After crystallization conditions are determined, crystallization of a larger amount of the protein can be achieved by methods known in the art, such as vapor diffusion or equilibrium dialysis. In vapor diffusion, a drop of protein solution is equilibrated against a larger reservoir of solution containing precipitant or another dehydrating agent. After sealing, the solution equilibrates to achieve supersaturating concentrations of proteins and thereby induce crystallization in the drop.

Equilibrium dialysis can be used for crystallization of proteins at low ionic strength. Under these conditions, a phenomenon known as "salting in" occurs, whereby the protein molecules achieve balance of electrostatic charges through interactions with other protein molecules. This method is particularly effective when the solubility of the protein is low at the lower ionic strength. Various apparatuses and methods are used, including microdiffusion cells in which a dialysis membrane is attached to the bottom of a capillary tube, which may be bent at its lower portion. The final crystallization condition is achieved by slowly changing the composition of the outer solution. A variation of these methods utilizes a concentration gradient equilibrium dialysis set up. Microdiffusion cells are available from commercial supplier such as Hampton Research (Laguna Niguel, Calif.).

Once crystallization is achieved, crystals characterized for purity (e.g. SDS-PAGE) and biological activity. Larger crystals (>0.2 mm) are preferred to increase the resolution of the X-ray diffraction, which is preferably on the order of 10-1.5 Angstroms. The selected crystals are subjected to X-ray diffraction, using a strong monochromatic X-ray source, such as a Synchrotron source or rotating anode generator, and the resulting X-ray diffraction patters are analyzed, using methods known in the art.

In one application β⁻-secretase amino acid sequence and/or X-ray diffraction data is recorded on computer readable medium, by which is meant any medium that can be read and directly accessed by a computer. These data may be used to model the enzyme, a subdomain thereof, or a ligand thereof. Computer algorithms useful for this application are publicly and commercially available.

The invention includes further cloning and expression of members of the aspartyl protease family described above, for example, by inserting polynucleotides encoding the proteins into standard expression vectors and transfecting appropriate host cells according to standard methods discussed below. Such expression vectors and cells expressing, for example, the human β-secretase enzyme described herein, have utility, for example, in producing components (purified enzyme or transfected cells) for the screening assays discussed herein. Such purified enzyme also has utility in providing starting materials for crystallization of the enzyme In accordance with the present invention, polynucleotide sequences which encode human β-secretase, splice variants, fragments of the protein, fusion proteins, or functional equivalents thereof, collectively referred to herein as "β-secretase," may be used in recombinant DNA molecules that direct the expression of β-secretase in appropriate host cells. Due to the inherent degeneracy of the genetic code, other nucleic acid sequences that encode substantially the same or a functionally equivalent amino acid sequences may be used to clone and express β-secretase. Such variations will be readily ascertainable to persons skilled in the art.

The polynucleotide sequences of the present invention can be engineered in order to alter a β-secretase coding sequence for a variety of reasons, including but not limited to, alterations that modify the cloning, processing and/or expression of the gene product. For example, alterations may be introduced using techniques which are well known in the art, e.g., site-directed mutagenesis, to insert new restriction sites, to alter glycosylation patterns, to change codon preference, to produce splice variants, etc. For example, it may be advantageous to produce β-secretase-encoding nucleotide sequences possessing non-naturally occurring codons. Codons preferred by a particular prokaryotic or eukaryotic host (Murray, E. et al., (1989) Nuc. Acids Res. 17:477-508) can be selected, for example, to increase the rate of β-secretase polypeptide expression or to produce recombinant RNA transcripts having desirable properties, such as a longer half-life, than transcripts produced from naturally occurring sequence. This may be particularly useful in producing recombinant enzyme in non-mammalian cells, such as bacterial, yeast, or insect cells. The present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook, et al., (supra).

The present invention also relates to host cells that are genetically engineered with vectors of the invention, and the production of proteins and polypeptides of the invention by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the β-secretase gene. The culture conditions, such as temperature, pH and the like, are those previously used with the host cell selected for expression, and will be apparent to those skilled in the art.

As described above, according to a preferred embodiment of the invention, host cells can be co-transfected with an enzyme substrate, such as with APP (such as wild type or Swedish mutation form), in order to measure activity in a cell environment. Such host cells are of particular utility in the screening assays of the present invention, particularly for screening for therapeutic agents that are able to traverse cell membranes.

The polynucleotides of the present invention may be included in any of a variety of expression vectors suitable for expressing a polypeptide. Such vectors include chromosomal, nonchromosomal and synthetic DNA sequence, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The DNA sequence in the expression vector is operatively linked to an appropriate transcription control sequence (promoter) to direct mRNA synthesis. Examples of such promoters include: CMV, LTR or SV40 promoter, the *E. coli* lac or trp promoter, the phage lambda PL promoter, and other promoters known to control expression of genes in prokaryotic or eukaryotic cells or their viruses. The expression vector also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as described above, as well as an appropriate promoter or control sequence, may be employed to transform an appropriate host to permit the host to express the protein. Examples of appropriate expression hosts include: bacterial cells, such as *E. coli, Streptomyces*, and *Salmonella typhimurium*; fungal cells, such as yeast; insect cells such as *Drosophila* and *Spodoptera* Sf9; mammalian cells such as CHO, COS, BHK, HEK 293 or Bowes melanoma; adenoviruses; plant cells, etc. It is understood that not all cells or cell lines will be capable of producing fully functional β-secretase. The selection of appropriate host is deemed to be within the scope of those skilled in the art from the teachings here. The invention is not limited by the host cells employed.

In bacterial systems, a number of expression vectors may be selected depending upon the use intended for β-secretase. For example, when large quantities of β-secretase or fragments thereof are needed for the induction of antibodies, vectors, which direct high level expression of fusion proteins that are readily purified, may be desirable. Such vectors include, but are not limited to, multifunctional *E. coli* cloning and expression vectors such as Bluescript® (Stratagene, La Jolla, Calif.), in which the β-secretase coding sequence may be ligated into the vector in-frame with sequences from the amino-terminal Met and the subsequent 7 residues of beta-galactosidase so that a hybrid protein is produced; pIN vectors (Van Heeke & Schuster (1989) J Biol. Chem. 264:5503-5509); pET vectors (Novagen, Madison, Wis.); and the like.

In the yeast *Saccharomyces cerevisiae* a number of vectors containing constitutive or inducible promoters such as alpha factor, alcohol oxidase and PGH may be used. For reviews, see Ausubel et al., (supra) and Grant et al. (1987; Methods in Enzymology 153:516-544).

In cases where plant expression vectors are used, the expression of a sequence encoding β-secretase may be driven by any of a number of promoters. For example, viral promoters such as the 35S and 19S promoters of CaMV (Brisson et al. (1984) Nature 310:511-514) may be used alone or in combination with the omega leader sequence from TMV (Takamatsu et al., (1987) EMBO J 6:307-311). Alternatively, plant promoters such as the small subunit of RUBISCO (Coruzzi et al., (1984) EMBO J 3:1671-1680; Broglie et al., (1984) Science 224:838-843); or heat shock promoters (Winter J and Sinibaldi R M (1991) Results. Probl. Cell Differ. 17:85-105) may be used. These constructs can be introduced into plant cells by direct DNA transformation or pathogen-mediated transfection. For reviews of such techniques, see Hobbs S or Murry L E (1992) in McGraw Hill Yearbook of Science and Technology, McGraw Hill, New York, N.Y., pp. 191-196; or Weissbach and Weissbach (1988) Methods for Plant Molecular Biology, Academic Press, New York, N.Y., pp. 421-463.

β-secretase may also be expressed in an insect system. Examples of such systems use baculovirus or *Autographa californica* nuclear polyhedrosis virus (AcNPV) as a vectors to express foreign genes in *Spodoptera frugiperda* Sf9 cells or in *Trichoplusia larvae*. The β-secretase coding sequence is cloned into a nonessential region of the virus, such as the polyhedrin gene, and placed under control of the polyhedrin promoter. With respect to AcNPV, successful insertion of Kv-SL coding sequence will render the polyhedrin gene inactive and produce recombinant virus lacking coat protein coat. The recombinant viruses are then used to infect *S. Frugiperda* cells or *Trichoplusa* larvae in which β-secretase is expressed (Smith et al., (1983) J Virol 46:584; Engelhard E K et al. (1994) Proc. Nat. Acad Sci 91:3224-3227).

In mammalian host cells, a number of viral-based expression systems may be utilized. In cases where an adenovirus is used as an expression vector, a β-secretase coding sequence may be ligated into the adenovirus transcription/translation complex consisting of the late promoter and tripartite leader sequence. Insertion in a nonessential E1 or E3 region of the viral genome will result in a viable virus capable of expressing the enzyme in infected host cells (Logan and Shenk (1984) Proc Natl Acad Sci 81:3655-3659). In addition, transcription enhancers, such as the rous sarcoma virus (RSV) enhancer, may be used to increase expression in mammalian host cells.

Specific initiation signals may also required for efficient translation of a β-secretase coding sequence. These signals include the ATG initiation codon and adjacent sequences. In cases where β-secretase coding sequence, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al., (1994) Results Probl Cell Differ 20:125-62; Bittner et al. (1987) Methods in Enzymol 153:516-544).

In a further embodiment, the present invention relates to host cells containing the above-described constructs. The host cell can be higher eukaryotic cell, such as a mammalian or insect cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, I. (1986) Basics Methods in Molecular Biology) or newer methods, including lipid transfection with "FUGENE" (Roche Molecular Biochemicals, Indianapolis, Ind.) or "EFFECTENE" (Quiagen, Valencia, Calif.), or other DNA carrier molecules. Cell-free translation systems can also be employed to produce polypeptides using RNAs derived from the DNA constructs of the present invention.

A host cell strain may be chosen for its ability to modulate the expression of the inserted sequences or to process the expressed protein n the desired fashion. Such modifications of the protein include, but are not limited to, acetylation, carboxylation, glycosylation, phosphorylation, lipidation and acylation. Post-translational processing which cleaves a "prepro" form of the protein may also be important for correct insertion, folding and/or function. For example, in the case of β-secretase, it is likely that the N-terminus is truncated, so that the protein begins at, for example, amino acid 22, 46 or 57-58. Different host cells such as CHO, HeLa, BHK, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression may be preferred. For example, cell lines that stably express β-secretase may be transformed using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clumps of stably transformed cells can be proliferated using tissue culture techniques appropriate to the cell type.

Host cells transformed with a nucleotide sequence encoding β-secretase may be cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding β-secretase can be designed with signal sequences which direct secretion of β-secretase polypeptide through a prokaryotic or eukaryotic cell membrane.

β-secretase may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a protease-cleavable polypeptide linker sequence between the purification domain and β-secretase is useful to facilitate purification. One such expression vector provides for expression of a fusion protein comprising β-secretase (e.g., a soluble β-secretase fragment) fused to a polyhistidine region separated by an enterokinase cleavage site. The histidine residues facilitate purification on IMIAC (immobilized metal ion affinity chromatography, as described in Porath et al. (1992) Protein Expression and Purification 3:263-281) while the enterokinase cleavage site provides a means for isolating β-secretase from the fusion protein. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathion-agarose in the case of GST-fusions) followed by elution in the presence of free ligand.

Following transformation of a suitable host strain and growth of the host strain to an appropriate cell density, the selected promoter is induced by appropriate means (e.g., temperature shift of chemical induction) and cells are cultured for an additional period. Cells are typically harvested by centrifugation, disrupted by physical or chemical means, and the resulting crude extract retained fur further purification. Microbial cells employed in expression of proteins can be disrupted by any convenient method, including freeze-thaw cycling, sonication, mechanical disruption, or use of cell lysing agents, or other methods, which are well known to those skilled in the art.

β-secretase can be recovered and purified from recombinant cell cultures by any of a number of methods well known in the art. Protein refolding steps can be used, as necessary, in completing configuration of the mature protein.

The present invention also includes methods for identifying molecules, such as synthetic drugs, antibodies, peptides, or other molecules, which have an inhibitory effect on the activity of β-secretase described herein, generally referred to as inhibitors, antagonists or blockers of the enzyme. Such an assay includes the steps of providing a human β-secretase, such as the β-secretase which comprises SEQ ID NOs:2-5, or more particularly in reference to the present invention, an isolated protein, about 450 amino acid residues in length, which includes an amino acid sequence that is at least 90% identical to SEQ ID NOs:2-5 including conservative substitutions thereof, which exhibits β-secretase activity, as described herein. The β-secretase enzyme is contacted with a test compound to determine whether it has a modulating effect on the activity of the enzyme, as discussed below, and selecting from test compounds capable of modulating β-secretase activity. In particular, inhibitory compounds (antagonists) are useful in the treatment of disease conditions associated with amyloid deposition, particularly Alzheimer's disease. Persons skilled in the art will understand that such assays may be conveniently transformed into kits.

Particularly useful screening assays employ cells which express both β-secretase and APP. Such cells can be made recombinantly by co-transfection of the cells with polynucleotides encoding the proteins, or can be made by transfecting a cell which naturally contains one of the proteins with the second protein. In a particular embodiment, such cells are grown up in multi-well culture dishes and are exposed to varying concentrations of a test compound or compounds for a pre-determined period of time, which can be determined empirically. Whole cell lysates, cultured media or cell membranes are assayed for β-secretase activity. Test compounds which significantly inhibit activity compared to control (as discussed below) are considered therapeutic candidates.

Isolated β-secretase, its ligand-binding, catalytic, or immunogenic fragments, or oligopeptides thereof, can be used for screening therapeutic compounds in any of a variety of drug screening techniques. The protein employed in such a test may be membrane-bound, free in solution, affixed to a solid support, borne on a cell surface, or located intracellularly. The formation of binding complexes between β-secretase and the agent being tested can be measured. Compounds that inhibit binding between β-secretase and its substrates, such as APP or APP fragments, may be detected in such an assay. Preferably, enzymatic activity will be monitored, and candidate compounds will be selected on the basis of ability to inhibit such activity. More specifically, a test compound will be considered as an inhibitor of β-secretase if the measured β-secretase activity is significantly lower than β-secretase activity measured in the absence of test compound. In this context, the term "significantly lower" means that in the presence of the test compound the enzyme displays an enzymatic activity which, when compared to enzymatic activity measured in the absence of test compound, is measurably lower, within the confidence limits of the assay method. Such measurements can be assessed by a change in $K_m$ and/or $V_{max2}$ single assay endpoint analysis, or any other method standard in the art.

For example, based upon previous studies, compounds can selected based on their ability to inhibit β-secretase activity in the MBP-C125$_{Swe}$ assay. Compounds that inhibit the enzyme activity at a concentration lower than about 50 μM can be selected for further screening.

The groups of compounds that are most likely candidates for inhibitor activity comprise a further aspect of the present invention. Previous studies have shown that the peptide compound described herein as P10-P4'staD→V (SEQ ID NO:6) is a reasonably potent inhibitor of the enzyme. Further studies based on this sequence and peptidomimetics of portions of this sequence have revealed a number of small molecule inhibitors.

Random libraries of peptides or other compounds can also be screened for suitability as β-secretase inhibitors. Combinatorial libraries can be produced for many types of compounds that can be synthesized in a step-by-step fashion. Such compounds including polypeptides, beta-turn mimetics, polysaccharides, phospholipids, hormones, prostaglandins, steroids, aromatic compounds, heterocyclic compounds, benzodizepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes).

Combinatorial libraries and other compounds are initially screened for suitability by determining their capacity to bind to, or preferably, to inhibit β-secretase activity in any of the assays described herein or otherwise known in the art. Compounds identified by such screens are then further analyzed for potency in such assays. Inhibitor compounds can then be tested for prophylactic and therapeutic efficacy in transgenic animals predisposed to any amyloidogenic disease, such as various rodents bearing a human APP-containing transgene, e.g., mice bearing a 717 mutation of APP described by Games et al., Nature 373:523-527, 1995 and Wadsworth et al. (U.S. Pat. No. 5,811,633, U.S. Pat. No. 5,604,131, U.S. Pat. No. 5,720,936), and mice bearing a Swedish mutation of APP such as described by McConlogue et al. (U.S. Pat. No. 5,612,486) and Hsiao et al. (U.S. Pat. No. 5,877,399); Staufenbiel et al., *Proc. Natl. Acad. Sci. USA* 94, 13287-13292 (1997); Struchler-Pierrat et al., *Proc. Natl. Acad. Sci. USA* 94, 13287-13292 (1997); Borchelt et al., *Neuron* 19, 939-945 (1997), all of which are incorporated herein by reference. Compounds or agents found to be efficacious and safe in such animal models will be further tested in standard toxicological assays. Compounds showing appropriate toxicological and pharmacokinetic profiles will be moved into human clinical trials for treatment of Alzheimer's disease and related diseases. The same screening approach can be used on other potential agents such as peptidomimetics described above.

In general, in selecting therapeutic compounds based on the foregoing assays, it is useful to determine whether the test compound has an acceptable toxicity profile, e.g., in a variety of in vitro cells and animal model(s). It may also be useful to search the tested and identified compound(s) against existing compounds databases to determine whether the compound or analogs thereof have been previously employed for pharmaceutical purposes, and if so, optimal routes of administration and dose ranges. Alternatively, routes of administration and dosage ranges can be determined empirically, using methods well known in the art (see, e.g., Benet, L. Z., et al. Pharmacokinetics in *Goodman & Gilman's The Pharmacological Basis of Therapeutics*, Ninth Edition, Harmdan, J. G., et al., Eds. McGraw-Hill, New York, 1966) applied to standard animal modes, such as a transgenic PDAPP animal model (e.g., Games, D., et al., Nature 373:523-527, 1995; Johnson-Wood, K., et al., Proc. Natl. Acad. Sci. USA 94:1550-1555, 1997). To optimize compound activity and/or specificity, it may be desirable to construct a library of near-neighbor analogs to search for analogs with greater specificity and/or activity. Methods for synthesizing near-neighbor and/or targeted compound libraries are well-known in the combinatorial library field.

The practitioner is also provided ample guidance for further refinement of the binding site of the enzyme, for example, by crystallizing the purified enzyme in accord with the methods provided herein. Noting the success in this area that has been enjoyed in the area of HIV protease inhibitor development, it is contemplated that such efforts will lead to further optimization of the test compounds described herein. With optimized compounds in hand, it is possible to define a compound pharmacophore, and further search existing pharmacophore databases, e.g., as provided by Tripos, to identify other compounds that may differ in 2-D structural formulae with the originally discovered compounds but which share a common pharmacophore structure and activity. Test compounds are assayed in any of the inhibitor assays described herein, at various stages in development. Therefore, the present invention includes β-secretase inhibitory agents discovered by any of the methods described herein, particularly the inhibitor assays and the crystallization/optimization protocols. Such inhibitory agents are therapeutic candidates for treatment of Alzheimer's disease, as well as other amyloidoses characterized by Aβ peptide deposition. The considerations concerning therapeutic index (toxicology), bioavailability and dosage discussed in Part B above are also important to consider with respect to these therapeutic candidates.

The present invention also provides methods of diagnosing individuals who carry mutations that provide enhanced β-secretase activity. For example, there are forms of familial Alzheimer's disease in which the underlying genetic disorder has yet to be recognized. Members of families possessing this genetic predisposition can be monitored for alterations in the nucleotide sequence that encodes β-secretase and/or promoter regions thereof, since it is apparent, in view of the teachings herein, that individuals who overexpress of the enzyme or possess catalytically more efficient forms of the enzyme would be likely to produce relatively more Aβ peptide. Support for this supposition is provided by the observation, reported herein, that the amount of β-secretase enzyme is rate limiting for production of Aβ in cells.

More specifically, persons suspected to have a predilection for developing for developing or who already have the disease, as well as members of the general population, may be screened by obtaining a sample of their cells, which may be blood cells or fibroblasts, for example, and testing the samples for the presence of genetic mutations in the β-secretase gene, in comparison to SEQ ID NO:1 described herein, for example. Alternatively or in addition, cells from such individuals can be tested for β-secretase activity. According to this embodiment, a particular enzyme preparation might be tested for increased affinity and/or Vmax with respect to a β-secretase substrate such as MBP-C125$_{Swe}$, as described herein, with comparisons made to the normal range of values measured in the general population. Individuals whose β-secretase activity is increased compared to normal values are susceptible to developing Alzheimer's disease or other amyloidogenic diseases involving deposition of Aβ peptide.

The following are provided for exemplification purposes only and are not intended to limit the scope of the invention described in broad terms above. All references cited in this disclosure are incorporated herein by reference.

EXAMPLES

Example 1

Preparation of BACE cDNA encoding BACE was inserted into a mammalian expression vector containing the CMV promoter to direct expression and the SV40 origin of replication to drive plasmid replication in COS cells. This expression cassette was transfected into COS A2 cells using FuGENE™ reagent (Roche Applied Science). Cell pellets were harvested 48 hours post transfection. Frozen cell pellets were homogenized in 20 mM HEPES, 2 mM EDTA, 5 µg/ml E-64, 10 µg/ml pepstatin, 1 mM phenylmethylsulfonyl fluoride, pH 7.5. A crude membrane fraction was recovered by centrifugation at 15,000×g for 40 minutes. The membrane pellet was extracted in 20 mM Tris, 2 mM EDTA, 0.2% Triton X-100, with 5 µg/ml E-64, 10 µg/ml pepstatin, 1 mM phenylmethylsulfonyl fluoride, pH 7.5. The extract was diluted with 4 volumes of SP buffer (20 mM sodium acetate, 2 mM EDTA, 0.2% Triton X-100, 60 mM sodium chloride, pH 5.0), and passed through a HiTrap™ SP cation exchange column (Amersham Biosciences). BACE was purified from the SP flow through by affinity chromatography on P$_{10}$-P$_4$'staV-Sepharose as described in Sinha et al, Nature, 1999. The affinity purified BACE was homogeneous by silver-stained SDS-polyacrylamide gels.

The human brain β-secretase used in this study was partially purified from Triton X-100 extracts of human brain membrane fractions, using WGA-agarose and SP cation exchange, as described previously in Sinha et al., Nature 1999. The SP flow-through was adjusted to pH 7.5 with Tris base and applied to a HiTrap™ Q column (Amersham Biosciences), which was eluted with a gradient of 50 mM to 450 mM sodium chloride in 20 mM Tris, pH 7.5, 2 mM EDTA, and 0.2% hydrogenated Triton X-100 (Calbiochem). Fractions containing β-secretase activity were pooled, aliquoted, and stored frozen.

Example 2

Preparation of BACE Extracellular Domain Constructs

The membrane truncated BACE C-terminal Flag epitope tag construct was engineered by PCR using a BACE cDNA template (Sinha et al.) with the following forward primer encoding a non-complementary BamHI site (lower case):

attattggatccGAGCCCAGAGGGCCCGAA,    (SEQ ID NO: 7)

and backward primer (plus a Flag tag sequence in lower case):

(SEQ ID NO: 8)
5'- gatatgtcgactcacttgtcatcgtcatctttataatcCTCATCTG
TCTGTGGAATGTTGTAGCC-3'.

Both backward primers included a SalI site to facilitate cloning of the PCR amplified fragment. The amplified fragment was cloned into pCRScript® (Stratagene) for DNA sequence verification. cDNA inserts encoding the 452 truncated constructs were subcloned into pIRES-EGFP (Clontech). The clones were co-transfected with pSV2Neo (Clonetech) into A293 cells, and antibiotic-resistant cells were selected and expanded in bulk. These bulk selected cells were cloned by limiting dilution, and also sorted by flow cytometry to yield enriched populations expressing medium or high levels of EGFP. Cells were grown in DMEM:F12 (1:1) supplemented with 50 µM ethanolamine, 10 nM sodium selenite, and 1 mM pyruvate for 16 to 48 hours. The conditioned medium was collected, diluted with 4 volumes of SP buffer containing 5 µg/ml E-64, 10 µg/ml pepstatin, 1 mM Phenylmethylsulfonyl fluoride, and passed through a HiTrap™ SP column. BACE was purified from the SP flow through by affinity chromatography as described above, except that the column was washed with 20 mM sodium acetate, 2 mM EDTA, 0.2% Triton X-100, pH 4.5, containing sequentially 125 mM, 250 mM, and 500 mM sodium chloride, before elution. Purified BACE was homogeneous by SDS-polyacrylamide gel electrophoresis.

Mature and proform of BACE were separated by immunoaffinity chromatography on immobilized 9H10, a monoclonal antibody directed against BACE prodomain. The proform was recovered by eluting the column with 50 mM acetic acid, 150 mM sodium chloride, 0.2% Triton X-100, at 0-4° C., immediately neutralizing the eluted fractions with Tris base. Under these conditions the activity of BACE was not affected. The identity of the eluted material as BACE proform was confirmed by Edman sequencing; only the sequence beginning at Thr$_{22}$ was observed.

Site directed mutagenesis of the N-linked glycosylation sites in BACE was carried out on the sequence verified 452Flag soluble BACE cDNA as the amplification template using the QuickChange® Site Directed Mutagenesis Kit (Stratagene) according to the manufacturer's instructions.

The sequences of the primers used for mutagenesis were as follows (sense strand only is shown):

N153Q
(SEQ ID NO: 9)
5'- ATCCCCCATGGCCCCcAaGTCACTGTGCGTGCCAAC

S174I
(SEQ ID NO: 10)
GACAAGTTCTTCATCAACGGCatCAACTGGGAAGGCATCCT

N223A
(SEQ ID NO: 11)
TGCTGGCTTCCCCCTCgcCCAGTCTGAAGTGCTGGCCT

N354S
(SEQ ID NO: 12)
TACCTAATGGGTGAGGTTACCAgCCAGTCCTTCCGCATCACCAT

Mutagenesis was performed sequentially as follows: N223A, N223A+S174I, N223A+S1174I+N1153Q, and finally, N223A+S174I+N153Q+N354S. All intermediates were sequence verified before proceeding with the next mutation. The mutants were cloned into the mammalian expression vector pCF for protein expression in HEK-293 cells.

Example 3

β-Secretase Assays

Peptide substrate MBP-C125$_{Swe}$ was used for all assays. MBP-C125$_{Swe}$ is a bacterial fusion protein containing maltose binding protein MBP fused to the C-terminal 125 amino acids of the Swedish variant (Lys$_{670}$Asn, Met$_{671}$Leu double mutation) of APP. Sinha et al (1999). The C-terminal 125 amino acids were cloned into the expression vector pMALc (New England Biolabs) and transfected into *E. coli*. The fusion proteins were induced and solubilized by sonication of the pelleted bacteria. The proteins were purified by affinity chromatography on amylose-agarose, made up to 3 M guanidine, and stored in 10 mM Tris, pH 7.5, 0.2% Triton X-100, and 0.15 M guanidine.

All digests were done with 0.02 μL BACE (Δ3, 0.69 μM; Δ2,3 0.77 μM; wild type 0.66 μM) at 37° C. in a total volume of 50 μL 0.06% Triton X-100 and 20 mM sodium acetate, pH 4.5. Samples were incubated with MBP-C125$_{Swe}$ substrate (10 μg/mL, 220 nM) for one hour. Digests were assayed in an ELISA assay, capturing with antibody to MBP and detecting with biotinylated Sw192, a neo-epitope specific antibody recognizing the free C-terminal leucine of the N-terminal product of β-secretase cleavage of the APP$_{Swe}$ sequence. See Seubert. P. et al. Nature 361:260-263 (1993), and Knops, J. et al. J. Biol. Chem. 270:2419-2422 (1995). Product was allowed to bind for 24 hours at 4° C., then quantitated with streptavidin-horse radish peroxidase. Biotinylated peptide corresponding to the N-terminal cleavage product was synthesized and used as a standard. The results are shown in Table 1.

TABLE 1

| Group Name | SampleID | Fluores | Value | Enzyme (μL/sample) | Enzyme (μM) | Cleavage Product (pM) | Substrate Conversion (%) | Activity (pM/h/ng enz) |
|---|---|---|---|---|---|---|---|---|
| delta 3 | B1 | 1582 | 125.82684 | 0.02 | 0.69 | 126 | 6.01% | 20,173 |
|  | B2 | 1564 | 124.12234 |  |  | SD = 8 |  | ±1,327 |
|  | B3 | 1512 | 119.21308 |  |  |  |  |  |
|  | B4 | 1470 | 115.26401 |  |  |  |  |  |
|  | B5 | 1692 | 136.30063 |  |  |  |  |  |
|  | B6 | 1673 | 134.48447 |  |  |  |  |  |
| delta 2, 3 | B7 | 1363 | 105.26829 | 0.02 | 0.77 | 109 | 5.19% | 15,753 |
|  | B8 | 1317 | 100.99977 |  |  | SD = 10 |  | ±1,442 |
|  | B9 | 1340 | 103.13187 |  |  |  |  |  |
|  | B10 | 1310 | 100.35172 |  |  |  |  |  |
|  | B11 | 1533 | 121.19301 |  |  |  |  |  |
|  | B12 | 1538 | 121.66495 |  |  |  |  |  |
| wild type | C1 | 1174 | 87.840448 | 0.02 | 0.66 | 85 | 4.05% | 14,308 |
|  | C2 | 1161 | 86.652416 |  |  | SD = 8 |  | ±1,363 |
|  | C3 | 1164 | 86.926455 |  |  |  |  |  |
|  | C4 | 1259 | 95.642317 |  |  |  |  |  |
|  | C5 | 1097 | 80.823741 |  |  |  |  |  |
|  | C6 | 994 | 71.513363 |  |  |  |  |  |
| delta 3 | G1 | 1577 | 125.3531 | 0.02 | 0.69 | 119 | 5.68% | 19,071 |
|  | G2 | 1520 | 119.96691 |  |  | SD = 11 |  | ±1,709 |
|  | G3 | 1344 | 103.50311 |  |  |  |  |  |
|  | G4 | 1401 | 108.80748 |  |  |  |  |  |
|  | G5 | 1577 | 125.3531 |  |  |  |  |  |
|  | G6 | 1636 | 130.95619 |  |  |  |  |  |
| delta 2, 3 | G7 | 1401 | 108.80748 | 0.02 | 0.77 | 108 | 5.16% | 15,662 |
|  | G8 | 1382 | 107.03641 |  |  | SD = 8 |  | ±933 |
|  | G9 | 1306 | 99.981592 |  |  |  |  |  |
|  | G10 | 1394 | 108.15464 |  |  |  |  |  |
|  | G11 | 1363 | 105.26829 |  |  |  |  |  |
|  | G12 | 1516 | 119.58993 |  |  |  |  |  |
| wild type | H1 | 1303 | 99.704079 | 0.02 | 0.66 | 90 | 4.30% | 15,177 |
|  | H2 | 1058 | 77.288274 |  |  | SD = 11 |  | ±1,826 |
|  | H3 | 1317 | 100.99977 |  |  |  |  |  |
|  | H4 | 1292 | 98.687158 |  |  |  |  |  |
|  | H5 | 1100 | 81.096214 |  |  |  |  |  |
|  | H6 | 1116 | 82.550642 |  |  |  |  |  |

FIG. 6 shows the results of the assays in $K_{cat}/K_m$ units (mM$^{-1}$sec$^{-1}$). These values were converted from the above data by the following equation: nM product/hr (ng enzyme)× 45 ng enzyme/pm enzx1/220 nM substratex1/3,660 sec/hr×50,000 nL/reaction.

Example 4

Expression of BACE Mutants Insect Cells Using Baculovirus Vectors

Mutant forms of BACE were produced in baculovirus in order to generate material for crystallographic efforts. To produce a minimally glycosylated, active form of soluble β-secretase, the S174I, N223A glycosylation mutant form of the enzyme with a histidine tag (Δ2,3-452H) was put into the baculovirus expression vector, pVL1392. In addition, proregion mutants were also made of soluble wt and glycosylation mutant enzymes (452H,NINL and Δ2,3-452H,NINL) to generate a homogeneously processed soluble enzyme. The NINL mutation changes the amino acid sequence at the cleavage site from $R_{42}L_{43}P_{44}R_{45}$ to NINL, to optimize for cleavage of the pro-region as described above.

The three mutants were transfected into Sf9 cells. Enzyme was purified from conditioned media of each transfection pool using the p10-p4'staD→V affinity resin. Expression and activity were demonstrated. Recombinant virus for Δ2,3-452H and 452H,NINL were further plaque-purified twice to generate viral stocks. Infections were then done in serum-free media for purification and characterization of each mutant form of BACE.

Coomassie-stained protein gel and western blot confirmed good expression of purified mutant enzymes. Enzyme activity was measured using the MBPc125$_{Swe}$ assay, and good activity was obtained for all samples tested.

N-terminal sequences was performed on the three purified enzymes. Two plaque-purified isolates of β452H showed that at least 90% of the material was proform (TQHGIRLPPR . . . ) with approximately 10% being fully processed enzyme (ET-DEEPEE . . . ). Δ2,3-452H material showed about ⅔ of the material as proform with the remaining ⅓ being fully processed. There were two predominant forms of the Δ2,3-452H, NINL material. One was the fully processed enzyme and the second form was cleaved just before the mutated processing site (NINLETDEEP . . . ). This is similar to what was seen in mammalian-expressed material.

Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. An isolated polynucleotide comprising a nucleotide sequence that encodes an isolated variant of a human beta-site APP cleaving enzyme having at least one of the following amino acid substitutions: S174I and N223A according to the numbering of SEQ ID NO:1, and wherein the variant is 95% identical to SEQ ID NOs: 2 or 3 and has APP cleaving activity.

2. The isolated polynucleotide of claim 1, wherein the variant has the amino acid substitution N223A according to the numbering of SEQ ID NO:1.

3. The isolated polynucleotide of claim 1, wherein the variant has amino acid substitutions S174I and N223A according to the numbering of SEQ ID NO:1.

4. The isolated polynucleotide of any one of claims 1-3 wherein the N terminus of the variant comprises amino acids NINL (SEQ ID NO:13) at positions 42-45 according to the numbering of SEQ ID NO:1.

5. An isolated polynucleotide encoding a polypeptide comprising SEQ ID NO:2.

6. An isolated polynucleotide encoding a polypeptide comprising SEQ ID NO:3.

7. An isolated polynucleotide encoding a protein comprising variant of a human beta-site APP cleaving enzyme that (i) is less than about 450 amino acid residues in length; (ii) is at least 95% identical to any one of SEQ ID NO:2 or SEQ ID NO:3, (iii) has at least one of the amino acid substitutions S174I and N223A according to the numbering of SEQ ID NO:1, and (iv) exhibits β-secretase activity.

8. An isolated polynucleotide comprising a sequence encoding a variant of a human beta-site APP cleaving enzyme having APP cleaving activity comprising a truncated variant of SEQ ID NO: 1 having at least one of the following amino acid substitutions: S174I and N223A according to the numbering of SEQ ID NO:1, wherein the variant has an N terminus residue selected from the group consisting of residues 22, 46, 58 and 63 according to the numbering of SEQ ID NO:1, and a C terminus at a residue selected from the group consisting of residues 451-501 according to the numbering of SEQ ID NO:1.

9. The variant of claim 8 wherein the C terminus is position 451 according to the numbering of SEQ ID NO:1.

10. The variant of claim 8 wherein the N terminus is position 46 according to the numbering of SEQ ID NO:1.

11. The variant of claim 8 wherein the N terminus includes amino acids NINL (SEQ ID NO:13) at positions 42-45 according to the numbering of SEQ ID NO:1.

12. A vector comprising the polynucleotide sequence of any one of claims 1, 5, 6, 7 or 8.

13. An isolated host cell comprising the vector of claim 12.

14. A method of producing a variant of a human beta-site APP cleaving enzyme comprising culturing a cell according to claim 13 under conditions to promote growth of the cell and expression of the variant, and purifying the variant.

* * * * *

SEQUENCE LISTING

```
<160> NUMBER OF SEQ ID NOS: 13

<210> SEQ ID NO 1
<211> LENGTH: 501
<212> TYPE: PRT
<213> ORGANISM: Homo sapiens
<220> FEATURE:
<221> NAME/KEY: MISC_FEATURE
<223> OTHER INFORMATION: Amino acid sequence of human wildtype BACE

<400> SEQUENCE: 1

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160
```

```
Ala Ala Ile Thr Glu Ser Asp Lys Phe Phe Ile Asn Gly Ser Asn Trp
            165                 170                 175

Glu Gly Ile Leu Gly Leu Ala Tyr Ala Glu Ile Ala Arg Pro Asp Asp
        180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445

Gln Thr Asp Glu Ser Thr Leu Met Thr Ile Ala Tyr Val Met Ala Ala
    450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500

<210> SEQ ID NO 2
<211> LENGTH: 406
<212> TYPE: PRT
<213> ORGANISM: Artificial
<220> FEATURE:
<223> OTHER INFORMATION: Human BACE with asparagine to alanine (N223A)
      mutation.

<400> SEQUENCE: 2

Glu Thr Asp Glu Glu Pro Glu Glu Pro Gly Arg Arg Gly Ser Phe Val
1               5                   10                  15
```

```
Glu Met Val Asp Asn Leu Arg Gly Lys Ser Gly Gln Gly Tyr Tyr Val
            20                  25                  30
Glu Met Thr Val Gly Ser Pro Pro Gln Thr Leu Asn Ile Leu Val Asp
        35                  40                  45
Thr Gly Ser Ser Asn Phe Ala Val Gly Ala Ala Pro His Pro Phe Leu
    50                  55                  60
His Arg Tyr Tyr Gln Arg Gln Leu Ser Ser Thr Tyr Arg Asp Leu Arg
65                  70                  75                  80
Lys Gly Val Tyr Val Pro Tyr Thr Gln Gly Lys Trp Glu Gly Glu Leu
                85                  90                  95
Gly Thr Asp Leu Val Ser Ile Pro His Gly Pro Asn Val Thr Val Arg
            100                 105                 110
Ala Asn Ile Ala Ala Ile Thr Glu Ser Asp Lys Phe Phe Ile Asn Gly
        115                 120                 125
Ser Asn Trp Glu Gly Ile Leu Gly Leu Ala Tyr Ala Glu Ile Ala Arg
    130                 135                 140
Pro Asp Ser Leu Glu Pro Phe Phe Asp Ser Leu Val Lys Gln Thr
145                 150                 155                 160
His Val Pro Asn Leu Phe Ser Leu Gln Leu Cys Gly Ala Gly Phe Pro
                165                 170                 175
Leu Ala Gln Ser Glu Val Leu Ala Ser Val Gly Gly Ser Met Ile Ile
            180                 185                 190
Gly Gly Ile Asp His Ser Leu Tyr Thr Gly Ser Leu Trp Tyr Thr Pro
        195                 200                 205
Ile Arg Arg Glu Trp Tyr Tyr Glu Val Ile Ile Val Arg Val Glu Ile
    210                 215                 220
Asn Gly Gln Asp Leu Lys Met Asp Cys Lys Glu Tyr Asn Tyr Asp Lys
225                 230                 235                 240
Ser Ile Val Asp Ser Gly Thr Thr Asn Leu Arg Leu Pro Lys Lys Val
                245                 250                 255
Phe Glu Ala Ala Val Lys Ser Ile Lys Ala Ala Ser Ser Thr Glu Lys
            260                 265                 270
Phe Pro Asp Gly Phe Trp Leu Gly Glu Gln Leu Val Cys Trp Gln Ala
        275                 280                 285
Gly Thr Thr Pro Trp Asn Ile Phe Pro Val Ile Ser Leu Tyr Leu Met
    290                 295                 300
Gly Glu Val Thr Asn Gln Ser Phe Arg Ile Thr Ile Leu Pro Gln Gln
305                 310                 315                 320
Tyr Leu Arg Pro Val Glu Asp Val Ala Thr Ser Gln Asp Asp Cys Tyr
                325                 330                 335
Lys Phe Ala Ile Ser Gln Ser Ser Thr Gly Thr Val Met Gly Ala Val
            340                 345                 350
Ile Met Glu Gly Phe Tyr Val Val Phe Asp Arg Ala Arg Lys Arg Ile
        355                 360                 365
Gly Phe Ala Val Ser Ala Cys His Val His Asp Glu Phe Arg Thr Ala
    370                 375                 380
Ala Val Glu Gly Pro Phe Val Thr Leu Asp Met Glu Asp Cys Gly Tyr
385                 390                 395                 400
Asn Ile Pro Gln Thr Asp
                405

<210> SEQ ID NO 3
<211> LENGTH: 406
```

```
<212> TYPE: PRT
<213> ORGANISM: Artificial
<220> FEATURE:
<223> OTHER INFORMATION: Human BACE with serine to isoleucine (S174I)
      and asparagine to alanine (N223A) mutations.

<400> SEQUENCE: 3

Glu Thr Asp Glu Glu Pro Glu Pro Gly Arg Arg Gly Ser Phe Val
1               5                   10                  15

Glu Met Val Asp Asn Leu Arg Gly Lys Ser Gly Gln Gly Tyr Tyr Val
                20                  25                  30

Glu Met Thr Val Gly Ser Pro Pro Gln Thr Leu Asn Ile Leu Val Asp
            35                  40                  45

Thr Gly Ser Ser Asn Phe Ala Val Gly Ala Ala Pro His Pro Phe Leu
        50                  55                  60

His Arg Tyr Tyr Gln Arg Gln Leu Ser Ser Thr Tyr Arg Asp Leu Arg
65              70                  75                  80

Lys Gly Val Tyr Val Pro Tyr Thr Gln Gly Lys Trp Glu Gly Glu Leu
                85                  90                  95

Gly Thr Asp Leu Val Ser Ile Pro His Gly Pro Asn Val Thr Val Arg
                100                 105                 110

Ala Asn Ile Ala Ala Ile Thr Glu Ser Asp Lys Phe Phe Ile Asn Gly
            115                 120                 125

Ile Asn Trp Glu Gly Ile Leu Gly Leu Ala Tyr Ala Glu Ile Ala Arg
        130                 135                 140

Pro Asp Asp Ser Leu Glu Pro Phe Phe Asp Ser Leu Val Lys Gln Thr
145                 150                 155                 160

His Val Pro Asn Leu Phe Ser Leu Gln Leu Cys Gly Ala Gly Phe Pro
                165                 170                 175

Leu Ala Gln Ser Glu Val Leu Ala Ser Val Gly Gly Ser Met Ile Ile
            180                 185                 190

Gly Gly Ile Asp His Ser Leu Tyr Thr Gly Ser Leu Trp Tyr Thr Pro
        195                 200                 205

Ile Arg Arg Glu Trp Tyr Tyr Glu Val Ile Ile Val Arg Val Glu Ile
210                 215                 220

Asn Gly Gln Asp Leu Lys Met Asp Cys Lys Glu Tyr Asn Tyr Asp Lys
225                 230                 235                 240

Ser Ile Val Asp Ser Gly Thr Thr Asn Leu Arg Leu Pro Lys Lys Val
                245                 250                 255

Phe Glu Ala Ala Val Lys Ser Ile Lys Ala Ala Ser Ser Thr Glu Lys
            260                 265                 270

Phe Pro Asp Gly Phe Trp Leu Gly Glu Gln Leu Val Cys Trp Gln Ala
        275                 280                 285

Gly Thr Thr Pro Trp Asn Ile Phe Pro Val Ile Ser Leu Tyr Leu Met
        290                 295                 300

Gly Glu Val Thr Asn Gln Ser Phe Arg Ile Thr Ile Leu Pro Gln Gln
305                 310                 315                 320

Tyr Leu Arg Pro Val Glu Asp Val Ala Thr Ser Gln Asp Asp Cys Tyr
                325                 330                 335

Lys Phe Ala Ile Ser Gln Ser Ser Thr Gly Thr Val Met Gly Ala Val
            340                 345                 350

Ile Met Glu Gly Phe Tyr Val Val Phe Asp Arg Ala Arg Lys Arg Ile
        355                 360                 365

Gly Phe Ala Val Ser Ala Cys His Val His Asp Glu Phe Arg Thr Ala
        370                 375                 380
```

```
Ala Val Glu Gly Pro Phe Val Thr Leu Asp Met Glu Asp Cys Gly Tyr
385                 390                 395                 400

Asn Ile Pro Gln Thr Asp
                405
```

<210> SEQ ID NO 4
<211> LENGTH: 406
<212> TYPE: PRT
<213> ORGANISM: Artificial
<220> FEATURE:
<223> OTHER INFORMATION: Human BACE with serine to isoleucine (S174I),
      asparagine to glutamine (N153Q) and asparagine to alanine (N223A)
      mutations.

<400> SEQUENCE: 4

```
Glu Thr Asp Glu Glu Pro Glu Glu Pro Gly Arg Arg Gly Ser Phe Val
1               5                   10                  15

Glu Met Val Asp Asn Leu Arg Gly Lys Ser Gly Gln Gly Tyr Tyr Val
                20                  25                  30

Glu Met Thr Val Gly Ser Pro Pro Gln Thr Leu Asn Ile Leu Val Asp
            35                  40                  45

Thr Gly Ser Ser Asn Phe Ala Val Gly Ala Ala Pro His Pro Phe Leu
        50                  55                  60

His Arg Tyr Tyr Gln Arg Gln Leu Ser Ser Thr Tyr Arg Asp Leu Arg
65                  70                  75                  80

Lys Gly Val Tyr Val Pro Tyr Thr Gln Gly Lys Trp Glu Gly Glu Leu
                85                  90                  95

Gly Thr Asp Leu Val Ser Ile Pro His Gly Pro Gln Val Thr Val Arg
                100                 105                 110

Ala Asn Ile Ala Ala Ile Thr Glu Ser Asp Lys Phe Phe Ile Asn Gly
            115                 120                 125

Ile Asn Trp Glu Gly Ile Leu Gly Leu Ala Tyr Ala Glu Ile Ala Arg
        130                 135                 140

Pro Asp Asp Ser Leu Glu Pro Phe Phe Asp Ser Leu Val Lys Gln Thr
145                 150                 155                 160

His Val Pro Asn Leu Phe Ser Leu Gln Leu Cys Gly Ala Gly Phe Pro
                165                 170                 175

Leu Ala Gln Ser Glu Val Leu Ala Ser Val Gly Gly Ser Met Ile Ile
                180                 185                 190

Gly Gly Ile Asp His Ser Leu Tyr Thr Gly Ser Leu Trp Tyr Thr Pro
            195                 200                 205

Ile Arg Arg Glu Trp Tyr Tyr Glu Val Ile Ile Val Arg Val Glu Ile
        210                 215                 220

Asn Gly Gln Asp Leu Lys Met Asp Cys Lys Glu Tyr Asn Tyr Asp Lys
225                 230                 235                 240

Ser Ile Val Asp Ser Gly Thr Thr Asn Leu Arg Leu Pro Lys Lys Val
                245                 250                 255

Phe Glu Ala Ala Val Lys Ser Ile Lys Ala Ala Ser Ser Thr Glu Lys
                260                 265                 270

Phe Pro Asp Gly Phe Trp Leu Gly Glu Gln Leu Val Cys Trp Gln Ala
            275                 280                 285

Gly Thr Thr Pro Trp Asn Ile Phe Pro Val Ile Ser Leu Tyr Leu Met
        290                 295                 300

Gly Glu Val Thr Asn Gln Ser Phe Arg Ile Thr Ile Leu Pro Gln Gln
305                 310                 315                 320
```

```
Tyr Leu Arg Pro Val Glu Asp Val Ala Thr Ser Gln Asp Cys Tyr
            325                 330                 335

Lys Phe Ala Ile Ser Gln Ser Ser Thr Gly Thr Val Met Gly Ala Val
            340                 345                 350

Ile Met Glu Gly Phe Tyr Val Val Phe Asp Arg Ala Arg Lys Arg Ile
        355                 360                 365

Gly Phe Ala Val Ser Ala Cys His Val His Asp Glu Phe Arg Thr Ala
    370                 375                 380

Ala Val Glu Gly Pro Phe Val Thr Leu Asp Met Glu Asp Cys Gly Tyr
385                 390                 395                 400

Asn Ile Pro Gln Thr Asp
            405

<210> SEQ ID NO 5
<211> LENGTH: 406
<212> TYPE: PRT
<213> ORGANISM: Artificial
<220> FEATURE:
<223> OTHER INFORMATION: Human BACE with serine to isoleucine (S174I),
      asparagine to glutamine (N153Q), asparagine to alanine (N223A) and
      asparagine to seine (N354S) mutations.

<400> SEQUENCE: 5

Glu Thr Asp Glu Glu Pro Glu Glu Pro Gly Arg Arg Gly Ser Phe Val
1               5                   10                  15

Glu Met Val Asp Asn Leu Arg Gly Lys Ser Gly Gln Gly Tyr Tyr Val
            20                  25                  30

Glu Met Thr Val Gly Ser Pro Pro Gln Thr Leu Asn Ile Leu Val Asp
        35                  40                  45

Thr Gly Ser Ser Asn Phe Ala Val Gly Ala Ala Pro His Pro Phe Leu
    50                  55                  60

His Arg Tyr Tyr Gln Arg Gln Leu Ser Ser Thr Tyr Arg Asp Leu Arg
65                  70                  75                  80

Lys Gly Val Tyr Val Pro Tyr Thr Gln Gly Lys Trp Glu Gly Glu Leu
                85                  90                  95

Gly Thr Asp Leu Val Ser Ile Pro His Gly Pro Gln Val Thr Val Arg
            100                 105                 110

Ala Asn Ile Ala Ala Ile Thr Glu Ser Asp Lys Phe Phe Ile Asn Gly
        115                 120                 125

Ile Asn Trp Glu Gly Ile Leu Gly Leu Ala Tyr Ala Glu Ile Ala Arg
    130                 135                 140

Pro Asp Asp Ser Leu Glu Pro Phe Phe Asp Ser Leu Val Lys Gln Thr
145                 150                 155                 160

His Val Pro Asn Leu Phe Ser Leu Gln Leu Cys Gly Ala Gly Phe Pro
                165                 170                 175

Leu Ala Gln Ser Glu Val Leu Ala Ser Val Gly Gly Ser Met Ile Ile
            180                 185                 190

Gly Gly Ile Asp His Ser Leu Tyr Thr Gly Ser Leu Trp Tyr Thr Pro
        195                 200                 205

Ile Arg Arg Glu Trp Tyr Tyr Glu Val Ile Ile Val Arg Val Glu Ile
    210                 215                 220

Asn Gly Gln Asp Leu Lys Met Asp Cys Lys Glu Tyr Asn Tyr Asp Lys
225                 230                 235                 240

Ser Ile Val Asp Ser Gly Thr Thr Asn Leu Arg Leu Pro Lys Lys Val
                245                 250                 255

Phe Glu Ala Ala Val Lys Ser Ile Lys Ala Ala Ser Ser Thr Glu Lys
```

-continued

```
                260                 265                 270
Phe Pro Asp Gly Phe Trp Leu Gly Glu Gln Leu Val Cys Trp Gln Ala
            275                 280                 285
Gly Thr Thr Pro Trp Asn Ile Phe Pro Val Ile Ser Leu Tyr Leu Met
        290                 295                 300
Gly Glu Val Thr Ser Gln Ser Phe Arg Ile Thr Ile Leu Pro Gln Gln
305                 310                 315                 320
Tyr Leu Arg Pro Val Glu Asp Val Ala Thr Ser Gln Asp Asp Cys Tyr
                325                 330                 335
Lys Phe Ala Ile Ser Gln Ser Ser Thr Gly Thr Val Met Gly Ala Val
            340                 345                 350
Ile Met Glu Gly Phe Tyr Val Val Phe Asp Arg Ala Arg Lys Arg Ile
        355                 360                 365
Gly Phe Ala Val Ser Ala Cys His Val His Asp Glu Phe Arg Thr Ala
    370                 375                 380
Ala Val Glu Gly Pro Phe Val Thr Leu Asp Met Glu Asp Cys Gly Tyr
385                 390                 395                 400
Asn Ile Pro Gln Thr Asp
                405
```

<210> SEQ ID NO 6
<211> LENGTH: 14
<212> TYPE: PRT
<213> ORGANISM: Artificial
<220> FEATURE:
<223> OTHER INFORMATION: Beta-secretase inhibitor.
<220> FEATURE:
<221> NAME/KEY: MISC_FEATURE
<222> LOCATION: (10)..(10)
<223> OTHER INFORMATION: Xaa is statine

<400> SEQUENCE: 6

```
Lys Thr Glu Glu Ile Ser Glu Val Asn Xaa Val Ala Glu Phe
1               5                   10
```

<210> SEQ ID NO 7
<211> LENGTH: 30
<212> TYPE: DNA
<213> ORGANISM: Artificial
<220> FEATURE:
<223> OTHER INFORMATION: Forward primer for making BACE extracellular
      constructs.

<400> SEQUENCE: 7
attattggat ccgagcccag agggcccgaa                                      30

<210> SEQ ID NO 8
<211> LENGTH: 65
<212> TYPE: DNA
<213> ORGANISM: Artificial
<220> FEATURE:
<223> OTHER INFORMATION: Backward primer for making BACE extracellular
      constructs.

<400> SEQUENCE: 8
gatatgtcga ctcacttgtc atcgtcatct ttataatcct catctgtctg tggaatgttg    60
tagcc                                                                65

<210> SEQ ID NO 9
<211> LENGTH: 36
<212> TYPE: DNA
<213> ORGANISM: Artificial

```
<220> FEATURE:
<223> OTHER INFORMATION: Sense primer for the N153Q mutation.

<400> SEQUENCE: 9
atcccccatg gcccccaagt cactgtgcgt gccaac                              36

<210> SEQ ID NO 10
<211> LENGTH: 41
<212> TYPE: DNA
<213> ORGANISM: Artificial
<220> FEATURE:
<223> OTHER INFORMATION: Sense primer for the S174I mutation.

<400> SEQUENCE: 10
gacaagttct tcatcaacgg catcaactgg gaaggcatcc t                        41

<210> SEQ ID NO 11
<211> LENGTH: 38
<212> TYPE: DNA
<213> ORGANISM: Artificial
<220> FEATURE:
<223> OTHER INFORMATION: Sense primer for the N223A mutation.

<400> SEQUENCE: 11
tgctggcttc cccctcgccc agtctgaagt gctggcct                            38

<210> SEQ ID NO 12
<211> LENGTH: 44
<212> TYPE: DNA
<213> ORGANISM: Artificial
<220> FEATURE:
<223> OTHER INFORMATION: Sense primer for the N354S mutation.

<400> SEQUENCE: 12
tacctaatgg gtgaggttac cagccagtcc ttccgcatca ccat                     44

<210> SEQ ID NO 13
<211> LENGTH: 4
<212> TYPE: PRT
<213> ORGANISM: Artificial
<220> FEATURE:
<223> OTHER INFORMATION: Synthetic

<400> SEQUENCE: 13

Asn Ile Asn Leu
 1
```